(12) United States Patent
Sung et al.

(10) Patent No.: US 12,102,324 B2
(45) Date of Patent: Oct. 1, 2024

(54) VASCULAR ANASTOMOTIC MEMBER COMPRISING SHAPE-MEMORY POLYMER

(71) Applicant: TMD LAB CO., LTD., Seoul (KR)

(72) Inventors: Hak-Joon Sung, Seoul (KR); Young Min Shin, Seoul (KR); Jung Bok Lee, Seoul (KR)

(73) Assignee: TMD LAB CO., LTD., Seoul (KR)

( * ) Notice: Subject to any disclaimer, the term of this patent is extended or adjusted under 35 U.S.C. 154(b) by 860 days.

(21) Appl. No.: 17/280,442

(22) PCT Filed: Oct. 2, 2019

(86) PCT No.: PCT/KR2019/012945
§ 371 (c)(1),
(2) Date: Mar. 26, 2021

(87) PCT Pub. No.: WO2020/071806
PCT Pub. Date: Apr. 9, 2020

(65) Prior Publication Data
US 2022/0000481 A1    Jan. 6, 2022

(30) Foreign Application Priority Data

Oct. 2, 2018  (KR) .......................... 10-2018-0117631

(51) Int. Cl.
| | |
|---|---|
| *A61B 17/11* | (2006.01) |
| *A61L 31/06* | (2006.01) |
| *A61B 17/00* | (2006.01) |

(52) U.S. Cl.
CPC .............. *A61B 17/11* (2013.01); *A61L 31/06* (2013.01); *A61B 2017/00871* (2013.01);
(Continued)

(58) Field of Classification Search
CPC ............ A61B 17/11; A61B 2017/1107; A61B 2017/1132; A61B 2017/1135;
(Continued)

(56) References Cited

U.S. PATENT DOCUMENTS

| | | | |
|---|---|---|---|
| 6,911,035 B1 * | 6/2005 | Blomme ................. | A61B 17/11 623/1.1 |
| 2015/0201943 A1 * | 7/2015 | Brooks .............. | A61B 17/1128 606/153 |

(Continued)

FOREIGN PATENT DOCUMENTS

| | | | | |
|---|---|---|---|---|
| EP | 3608346 A1 * | 2/2020 | .............. | A61F 2/06 |
| JP | 2018-522992 A | 8/2018 | | |

(Continued)

OTHER PUBLICATIONS

Office Action from corresponding Japanese Patent Application No. 2021-544081, dated Apr. 26, 2022.
(Continued)

*Primary Examiner* — Diane D Yabut
*Assistant Examiner* — Christina C Lauer
(74) *Attorney, Agent, or Firm* — Harness, Dickey & Pierce, P.L.C.

(57) ABSTRACT

The present invention relates to an artificial blood vessel comprising a shape-memory polymer, and a vascular anastomotic member formed of a shape-memory polymer. An artificial blood vessel according to an embodiment of the present invention comprises a shape-memory polymer including photo-crosslinkable functional groups, the artificial blood vessel thus provided having a fusion point suitable for in vivo transplantation. Also, provided is a vascular anastomotic member which comprises a shape-memory (Continued)

polymer including photo-crosslinkable functional groups, and thus has a fusion point suitable for in vivo transplantation.

17 Claims, 27 Drawing Sheets

(52) U.S. Cl.
CPC .............. *A61B 2017/1107* (2013.01); *A61B 2017/1135* (2013.01); *A61L 2300/42* (2013.01)

(58) Field of Classification Search
CPC .......... C08L 33/14; C08L 67/04; C08L 67/06; C08L 2201/12; C08G 65/2615
See application file for complete search history.

(56) References Cited

U.S. PATENT DOCUMENTS

| | | | |
|---|---|---|---|
| 2016/0095599 A1* | 4/2016 | Jose | A61B 17/11 606/154 |
| 2018/0126046 A1 | 5/2018 | Sung et al. | |

FOREIGN PATENT DOCUMENTS

| | | |
|---|---|---|
| KR | 10-1748551 B1 | 6/2017 |
| KR | 10-1906472 B1 | 10/2018 |
| WO | WO-2018186575 A1 | 10/2018 |

OTHER PUBLICATIONS

International Search Report from corresponding PCT Application No. PCT/KR2019/012945, dated Jan. 10, 2020.

Shen, H. et al.; "Cross-linking and damping properties of poly(caprolactone-co-glycidyl methacrylate)", Polymer Journal, 2014, vol. 46, pp. 598-608.

Zhao, S-P, et al.; Synthesis and Properties of Photopolymerized pH-Sensitive Hydrogels of Methacrylic Acid and Biodegradable PEG-b-PCL Macromer, Iranian Polymer Journal, 2011, vol. 20, No. 4, pp. 329-340.

Bicak, N., et al.; "Synthesis of new polyesters with methacrylate pendant groups", Polymer Bulletin, 2006, vol. 56, No. 1, pp. 87-93.

Shin, Y. C. el al. Development of a Shape-Memory Tube to Prevent Vascular Stenosis. Adv. Mater. [First published] Aug. 27, 2019, vol. 31, No. 41, 1904476, inner pp. 1-8.

* cited by examiner

VASCULAR ANASTOMOTIC MEMBER COMPRISING SHAPE-MEMORY POLYMER

CROSS-REFERENCE TO RELATED APPLICATIONS

This application is a national phase application of PCT Application No. PCT/KR2019/012945, filed on Oct. 2, 2019, which claims benefit of Korean Patent Application No. 10-2018-0117631, filed Oct. 2, 2018. The entire disclosure of the applications identified in this paragraph are incorporated herein by references.

TECHNICAL FIELD

The present invention relates to a vascular anastomotic member including a shape-memory polymer.

BACKGROUND

With rapid urbanization, due to people's lack of exercise and the prevalence of westernized dietary habits, vascular obstruction diseases in which blood vessels in the human body are narrowed or blocked to a considerable degree are gradually increasing. Particularly, most heart diseases may be caused by ischemia which is the blockage of blood vessels providing nutrients and oxygen to the heart, and include, representatively, myocardial infarction and angina.

Surgical therapy can be often applied to treat occluded or almost occluded blood vessels. For example, after cutting a site where a vascular occlusion has progressed, a vascular anastomosis, which is a procedure that connects cut blood vessels, may be used. In addition, in addition to the treatment of these vascular occlusive diseases, in organ transplantation or a surgical procedure for connecting cut blood vessels, a vascular anastomosis may be performed.

In addition to the treatment of vascular occlusive diseases of the heart as described above, in reconstructive surgery with flaps or a vascular anastomosis, a method of securing the field of vision during surgery with a microscope or a high magnifying glass and manually suturing one by one with a suture by a microsurgery specialist is used. Therefore, such suturing can be performed only by a highly skilled specialist, and it takes a lot of time and efforts to train these specialists.

In addition, for the vascular anastomosis with a suture, local or free flaps are required for reconstruction after tissue removal surgery such as surgery for various types of cancer, and particularly, in the case of free flaps, since microvascular anastomosis that connects blood vessels is essential, increased surgery time and costs may be problematic.

Therefore, numerous vascular anastomosis devices have been developed to avoid manually suturing blood vessels one by one with a suture. Among these, devices that can easily perform end-to-end anastomosis for blood vessels are disclosed in the U.S. Pat. Nos. 3,774,615, 4,214,586 and 4,917,087, and as an example that has already been commercialized, there is a microvascular anastomotic coupler (Synovis Micro Companies Alliance, USA).

In U.S. Pat. No. 3,774,615, a device for connecting disconnected vessels without surgery is disclosed. However, this device does not completely fix blood vessels at an anastomotic site, and it is difficult to evenly adhere two cut blood vessels by moving around them, and due to a very small area where the disconnected parts meet each other, there is a possibility of anastomosis not working properly leading to blood leakage.

In addition, in U.S. Pat. No. 4,214,586, like U.S. Pat. No. 3,774,615, a device for firmly fixing disconnected ends of blood vessels is disclosed, and this device has a problem in that there is a very small area where the disconnected parts of vessels meet, and thus anastomosis may not be properly performed.

In addition, in U.S. Pat. No. 4,917,087, a fixed tubular vascular anastomotic device is disclosed. While this device is capable of being used in an end-to-end or end-to-side anastomosis, it is not effective because it can only be used when two blood vessels have the same diameter, after anastomosis of inner layers, a fixing force associated with a part of the inner layer is weak, and thus the layer tends to return to a state before anastomosis.

That is, most of the conventional vascular anastomotic devices described above fix blood vessels at a specific site after eversion, and physically anastomize them, and due to the characteristics of blood vessels, such a physical anastomotic method through eversion of a blood vessel can be used for veins with relatively thin muscle tissue in a blood vessel wall, but cannot be used for arteries with relatively thick muscle tissue in a blood vessel wall. Particularly, since the procedure through physical vascular eversion may not be performed on patients with vascular diseases, its applications are considerably limited.

Meanwhile, recently, research on a biocompatible synthetic polymer to be applied to human blood vessels or organs is actively being conducted.

More specifically, the synthetic polymers to be applied in human blood vessels or organs include poly(lactic acid) (PLA), poly(glycolic acid) (PGA), poly(lactic-co-glycolic acid) (PLGA), and poly(ε-caprolactone) (PCL).

Among these, PCL is known as a biodegradable polymer, which is biocompatible and approved by the US FDA for biomedical applications enabling photo-crosslinking and chemical modification into a shape-memory polymer (SMP).

However, the melting temperature ($T_m$) of PCL is 45 to 65° C., which is too high to be applied to applied physiological instruments (37° C.). Accordingly, a shape-memory polymer such as PCL limits the clinical ability to treat blood vessels and other symptoms. In addition, the use of other shape-memory polymers for treatment is limited since a methacrylate functionalization step or a monomer synthesis step is required.

Therefore, it is necessary to develop a shape-memory polymer for vascular therapy, which is relatively non-invasive, painless and applied at low cost, and particularly, to develop a shape-memory polymer that can be used as a medical instrument or material having a melting temperature suitable for being used in artificial blood vessels or vascular anastomosis.

SUMMARY

Technical Problem

The present invention is directed to providing a vascular anastomotic member including a shape-memory polymer, which has a melting temperature suitable for in vivo transplantation.

The present invention is also directed to providing a vascular anastomotic member, which may easily perform vascular anastomosis, and minimize an adverse effect on blood flow by preventing damage caused by vascular eversion.

Technical Solution

To solve the above-described problem,
one aspect of the present invention provides a vascular anastomotic member including a shape-memory polymer represented by Formula 1:

[Formula 1]

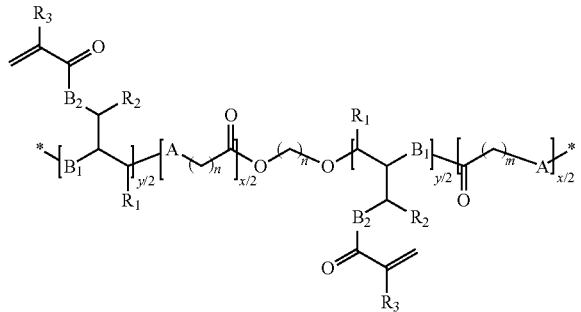

In Formula 1,
$R_1$, $R_2$ and $R_3$ are each independently hydrogen (H) or a C1 to C6 alkyl group,
m and n are each independently an integer of 1 to 20,
A, $B_1$ and $B_2$ are each independently oxygen (O) or sulfur (S),
x and y represent mol % of a repeat unit,
x+y is 100, and x is 80 to 95.

Advantageous Effects

An artificial vessel according to one embodiment of the present invention can provide a vascular anastomotic member having a melting temperature suitable for in vivo transplantation, which includes a shape-memory polymer having a crosslinkable functional group.

Particularly, the vascular anastomotic member according to one embodiment of the present invention can rapidly and conveniently perform vascular anastomosis without the use of a suture.

DETAILED DESCRIPTION

Figure 1:
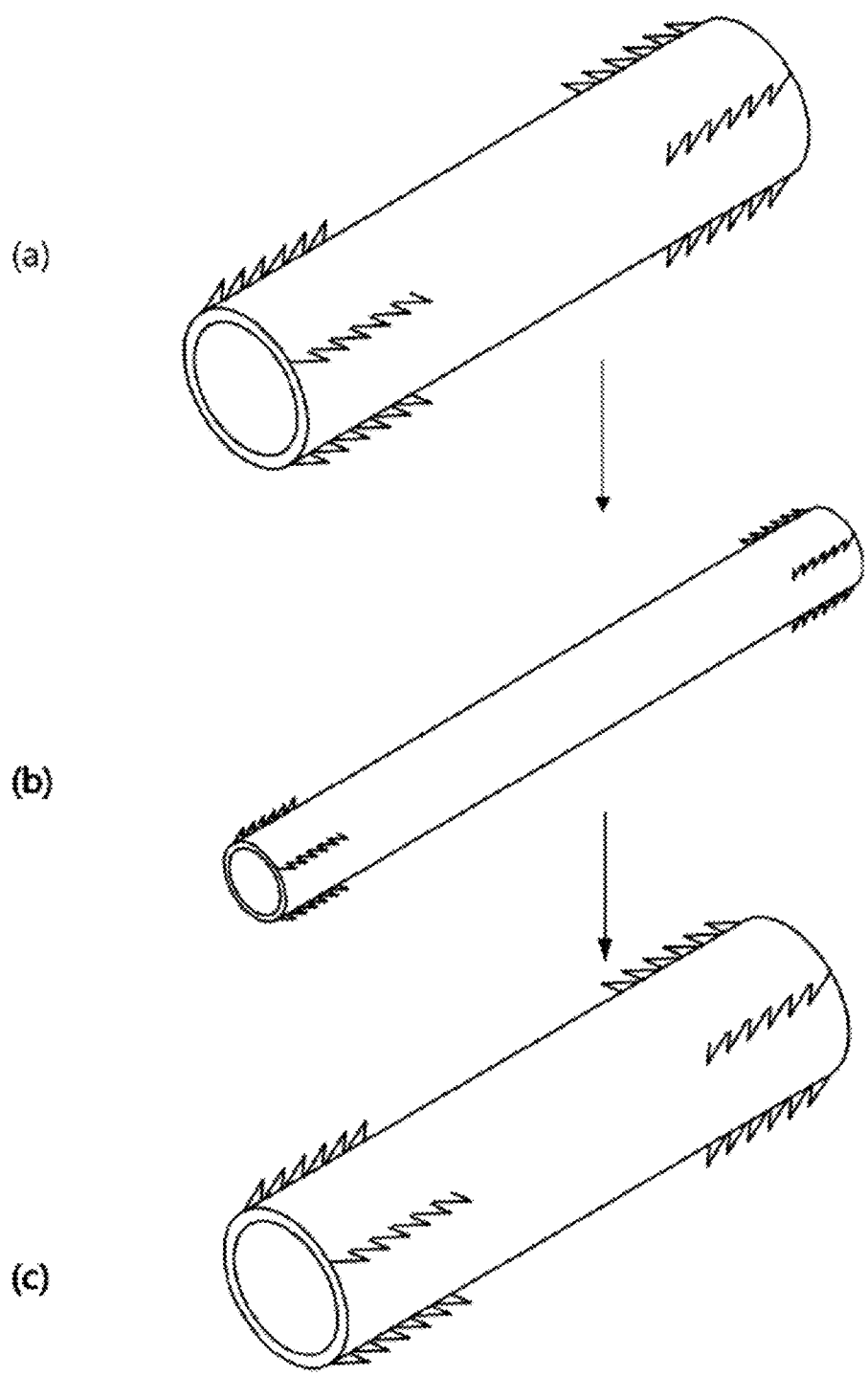
FIG. 1 shows a process of the morphological change in a vascular anastomotic member according to the present invention ((a) initial shape, (b) temporary shape (deformed state), (c) permanent shape (recovered state)).

The present invention may have various modifications and various examples, and thus specific examples are illustrated in the drawings and described in detail in the detailed description.

However, it should be understood that the present invention is not limited to specific embodiments, and includes all modifications, equivalents or alternatives within the idea and technical scope of the present invention.

The terms "comprise", "have" or "consist of" used herein designate the presence of characteristics, numbers, steps, actions, components or members described in the specification or a combination thereof, and it should be understood that the possibility of the presence or addition of one or more other characteristics, numbers, steps, actions, components, members or a combination thereof is not excluded in advance.

In addition, the accompanying drawings in the present invention should be understood as being enlarged or reduced for convenience of description.

Hereinafter, embodiments will be described in detail with reference to the accompanying drawings. However, the same reference numbers will be assigned to the same or corresponding elements regardless of the figure number, and the overlapping descriptions thereof will be omitted.

The "anastomosis" used herein refers to a state in which blood vessels are connected to each other, the "vascular anastomotic member" refers to an anastomotic member for connecting blood vessels by suturing or adhesion to maintain the connection of the blood vessels. In the present invention, the vascular anastomotic member is the generally referred to as a "graft material" which is directly transplanted into a blood vessel. In addition, the "first blood vessel" and "second blood vessel" may refer to blood vessels into which a tubular vascular anastomotic member is inserted, and cut blood vessels each having ends. Further, the vascular anastomotic member may include an artificial blood vessel referring to an artificial organ connecting the flow of blood instead of a damaged blood vessel.

Meanwhile, the first blood vessel and the second blood vessel may have the same diameter, but as a specific aspect, the diameters of the first blood vessel and the second blood vessel may be different from each other. That is, according to the blood flow from the first direction to the second direction, the diameter of the vascular anastomotic member of the present invention may be gradually increased. In the specification, the vascular anastomotic member having the above-mentioned shape may be referred to as a "diffuser-type model."

Here, the "first direction" and "second direction" may refer to the direction of blood flow. More specifically, the "from the first direction to the second direction" may refer to the direction of a blood flow, and the direction of blood flowing from the first blood vessel to the second blood vessel.

The vascular anastomotic member according to one embodiment of the present invention may include a shape-memory polymer.

The "shape-memory polymer (SMP)" used herein refers to a polymer that "remembers" an initial polymer shape and return to its original shape from a shape changed by a proper stimulus. In other words, the SMP is a polymer that goes through three steps of (1) imparting a permanent shape (initial shape) by processing, (2) changing the permanent shape into a temporary shape at low temperature, and (3) recovering the original permanent shape by an external stimulus (temperature).

In the present invention, the stimulus may be "temperature", and specifically, the SMP may return to the original shape when being heated to a transition temperature (glass transition temperature or melting temperature) or more. That is, the "melting temperature" used herein may refer to a temperature at which the SMP returns to the original shape (initial shape), not the melting point of the polymer.

Meanwhile, the melting temperature of the SMP according to one embodiment of the present invention may be 30 to 48° C. on average, and by crosslinking, the melting temperature may decrease. Specifically, the melting temperature of the SMP after crosslinking may be 28 to 42° C. on average. That is, as the artificial blood vessel or vascular anastomotic member of the present invention includes the above-described SMP, the SMP may return to the original shape (initial shape) at a temperature of 28 to 42° C. or more on average. Accordingly, the vascular anastomotic member according to the present invention may be suitable for in vivo transplantation. Here, crosslinking may be photo-crosslinking or thermal crosslinking. As an example, a shape may be imparted to the vascular anastomotic member by inducing photo-crosslinking to a synthesized SMP, and the melting temperature of the SMP may be lowered to 28 to 42° C.

For a SMP, the "strain" refers to a rate indicating how much a shape changes when the SMP is restored to an initial shape from a temporary shape and thus maintained in a permanent shape, and a rate of changing from a temporary shape to a permanent shape. In addition, the "strain recovery rate" refers to a recovery rate when SMP is restored to the initial original shape before being changed from the temporary shape by a physical force, and a ratio of the initial shape and the permanent shape. The strain in the present invention may be changed by a ratio or condition (temperature, UV, etc.) of monomers included in a SMP, and specifically, 5 to 350%. In addition, the strain recovery rate may be 90% or more.

In addition, the artificial blood vessel and vascular anastomotic member according to one embodiment of the present invention may consist of a biodegradable SMP. Here, the "biodegradable" describes a property of being decomposed by an enzyme secreted by microorganisms in nature, and being decomposed in a living body without almost no inflammation when applied to a living body. In addition, the "biodegradable SMP" refers to a polymer material that is decomposed in the human body over time to be absorbed in the human body, and capable of changing a shape by a temperature change. That is, the biodegradable SMP refers to a polymer material having biodegradability among SMPs capable of changing shapes by a temperature change.

In addition, the "front side" used herein means a front side on a drawing, indicating a side that is not in contact with a blood vessel, and the "back" used herein means a back side on a drawing, indicating a side that is in contact with a blood vessel.

Further, the "end" used herein means an end part, indicating the end of a blood vessel, and specifically, a disconnected or cut part of a blood vessel. The "side" means a lateral part, and the side of a blood vessel.

Moreover, the "end-to-end" used herein refers to connection of an end of a first blood vessel to an end of a second blood vessel, and the "end-to-end end anastomosis" refers to anastomosis that connects an end of the first blood vessel to an end of the second blood vessel. In addition, the "end-to-side" refers to anastomosis that connects an end of the first blood vessel to a side of the second blood vessel.

Hereinafter, the present invention will be described in detail.

The present invention is to provide a vascular anastomotic member including a SMP with a melting temperature suitable for in vivo transplantation.

Further, the present invention is to provide a vascular anastomotic member that can easily perform vascular anastomosis, and minimize an adverse effect on blood flow by preventing damage by vascular eversion.

In one embodiment of the present invention,
a vascular anastomotic member including a SMP represented by Formula 1 below is provided:

[Formula 1]

In Formula 1,
$R_1$, $R_2$ and $R_3$ each independently hydrogen (H) or a C1 to C6 alkyl group,
m and n are each independently an integer of 1 to 20,
A, $B_1$ and $B_2$ are each independently oxygen (O) or sulfur (S),
x and y represent mol % of a repeat unit,
x+y is 100, and x is 80 to 95.
Specifically,
in Formula 1,
$R_1$, $R_2$ and $R_3$ are each independently hydrogen (H) or a methyl group ($CH_3$—),
m and n are each independently an integer of 3 to 12,
A, $B_1$ and $B_2$ are each independently oxygen (O),
x and y represent mol % of a repeat unit,
x+y is 100, and x is 88 to 94.
More specifically,
$R_1$, $R_2$ and $R_3$ are each independently hydrogen (H),
m and n are each independently an integer of 5 to 6,
A, $B_1$ and $B_2$ are each independently oxygen (O),
x and y represent mol % of a repeat unit,
x+y is 100, and x is 88 to 94.
Formula 1 may be represented by Formula 2 below:

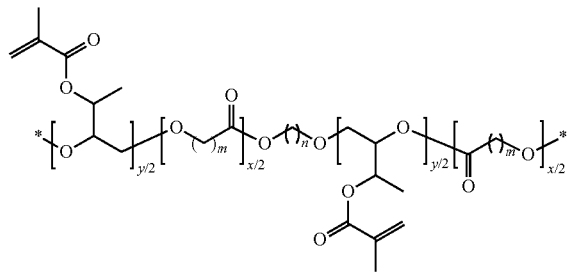

[Formula 2]

m and n are each independently an integer of 1 to 20,
x and y represent mol % of a repeat unit,
x+y is 100, and x is 80 to 95.

The shape-memory polymer according to the present invention may have the structure of a copolymer prepared by polymerizing a ε-caprolactone monomer and an acryl monomer having a glycidyl group. For example, the shape-memory polymer may have the structure of a polymer [PCL-co-PGMA)] prepared by polymerizing a ε-caprolactone monomer (CL; caprolactone) and glycidyl methacrylate (GMA).

In the above-described shape-memory polymer according to the present invention, the ε-caprolactone monomer and the acryl monomer are not particularly limited in the order of arrangement, and may be arranged alternatively, randomly or in blocks.

In addition, a hydroxyl group may be bound to an end of a copolymer having the unit of Formula 1 or 2. The copolymer in which a hydroxyl group is bound to its end may be prepared through polymerization using an initiator in which a hydroxyl group is bound to its end.

Further, the glycidyl group included in the acryl monomer may be a crosslinkable functional group, a photo-crosslinkable functional group or a thermal crosslinkable functional group.

Meanwhile, a melting temperature and the like may be adjusted according to the amounts of the ε-caprolactone monomer and the acryl monomer having a glycidyl group, which constitute the shape-memory polymer according to one embodiment of the present invention.

More specifically, in Formula 1 or 2, x and y may represent mol % of a repeat unit, x+y may be 100, and x may be 80 to 95 or 88 to 94.

Here, mol % represents a ratio of repeat units of x and y, and specifically, a molar ratio. As an example, in PCL-co-PGMA, mol % may represent a molar ratio of repeat units of PCL and PGMA.

For reference, in Formula 1, when x is less than 80, after crosslinking of the SMP, the melting temperature may be decreased to less than 28° C., leading to a shape change at room temperature, and therefore, such SMP may be difficult to be applied to the human body. When x is more than 95, the melting temperature after crosslinking is more than 42° C., leading to an increase in phase transition temperature of the SMP for shape recovery, and therefore, such SMP may be difficult to be applied to the human body temperature (37° C.).

The SMP may have a melting temperature of 30 to 48° C., and when crosslinked, the melting temperature may be lower than the above-mentioned temperature.

More specifically, the melting temperature of the SMP after crosslinking may be 28 to 42° C. on average.

For reference, as described above, when the melting temperature of the crosslinked shape-memory polymer is less than 28° C., the shape of a material may be changed at room temperature, so that it is limited in application as a physiologically applied instrument, and when the melting temperature of the crosslinked shape-memory polymer is more than 42° C., the shape memory ability of the material may be reduced as a strain recovery rate is 90% or less.

Particularly, since the shape-memory polymer of the present invention after crosslinking exhibits a strain recovery rate of 90% or more at 28 to 42° C. or more, which includes a body temperature, it can be used in various applications such as physiologically applied instruments or medical materials, for example, the vascular anastomotic member of the present invention.

Meanwhile, the above-described SMP may be a biodegradable SMP. More specifically, the "biodegradable SMP" refers to a polymer material that can be degraded in the human body over time to be absorbed in the human body and change its shape by a temperature change, and a polymer that can be decomposed and absorbed in the human body by changing its shape due to a temperature change. For example, the biodegradable SMP may be a biodegradable SMP regardless of before and after crosslinking.

Particularly, as the artificial blood vessel according to the present invention is formed of a biodegradable SMP, it is possible to minimize various causes that can adversely affect blood flow according to a physical change of a blood vessel by giving an external change to the artificial blood vessel, rather than the physical change to a human blood vessel, and when a patient in a growing phase undergoes a procedure using an artificial blood vessel consisting of material semi-permanently remaining in the human body, the growth of a blood vessel may be suppressed, and the problem of repetitive vascular procedures after a certain period of time may be solved.

The shape-memory polymer represented by Formula 1 may be prepared by polymerizing the shape-memory polymer of Formula 1 by a reaction of a compound of Formula 3, a compound of Formula 4, and a compound of Formula 4, but the present invention is not limited thereto.

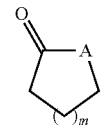
[Formula 3]

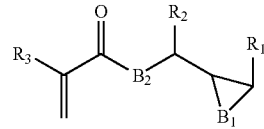
[Formula 4]

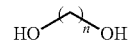
[Formula 5]

In Formulas 3 to 5,
$R_1$, $R_2$ and $R_3$ are each independently hydrogen (H) or a C1 to C6 alky group ($C_nH_{2n+1}$—),
m and n are each independently an integer of 1 to 20, and
A, $B_1$ and $B_2$ are each independently oxygen (O) or sulfur (S).

As described above, the shape-memory polymer according to the present invention may have a structure of the copolymer prepared by polymerizing a ε-caprolactone monomer and an acryl monomer having a glycidyl group. For example, the shape-memory polymer may have a structure of a copolymer [PCL-co-PGMA)] prepared by polymerizing a ε-caprolactone monomer (CL; caprolactone) and glycidyl methacrylate (GMA).

Here, the compound of Formula 5 may be an initiator used in polymerization, as an example, 1,6-hexanediol may be used as an initiator. Particularly, in polymerization, the compound of Formula 3 and the compound of Formula 4 may be condensation-polymerized based on the compound of Formula 5, and arranged alternatively, randomly or in blocks based on the compound of Formula 5.

As an example, in a method of preparing a shape-memory polymer having the structure of a copolymer [PCL-co-PGMA)], first, an initiator 1,6-hexanediol and ε-caprolactone (CL) and glycidyl methacrylate (GMA), which are monomers, may be mixed in a suitable molar ratio, and when determined to be thermally stable, a catalyst compound is added, and then copolymerization is performed at a reaction temperature of 80 to 140° C.

Subsequently, the polymerized product may be purified through washing and filtration and then dried, thereby preparing a shape-memory polymer of Formula 1.

In one example, a SMP polymerization mechanism of PCL-co-PGMA according to one embodiment of the present invention is as follows.

[Reaction Scheme 1]

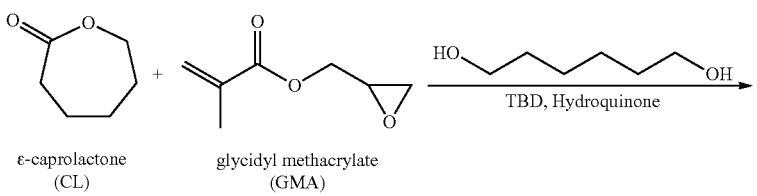

ε-caprolactone (CL)    glycidyl methacrylate (GMA)

-continued

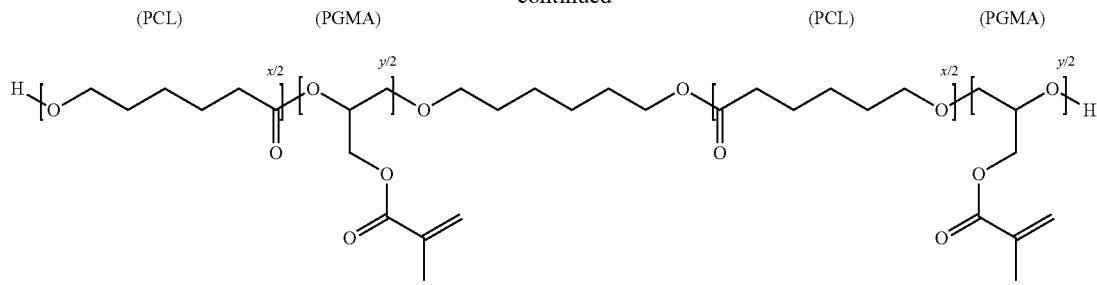

As shown above, the method of preparing a shape-memory polymer according to one embodiment of the present invention includes copolymerizing ε-caprolactone (CL) and glycidyl methacrylate (GMA) as monomers.

In addition, the catalyst may be 1,5,7-triazabicyclo[4.4.0]dec-5-ene (TBD), tin(II) (2-ethylhexanoate), trimethylopropane tris(3-mercaptopropionate) or zinc succinate, and as an example, since TBD exhibits a high yield in a low amount, it is able to be used as a catalyst.

The amount of a catalyst used herein may be 0.5 to 1 mol with respect to a starting material, but the present invention is not limited thereto.

Particularly, TBD is a material that can induce simultaneous ring opening polymerization of two monomers (CL and GMA), and has an effect of reducing the synthesis time of a SMP.

At the time point when a polymerization conversion rate is almost zero, that is, in the initial reaction, a polymerization inhibitor as well as a HD initiator may be added before the addition of a GMA monomer to inhibit a reaction between GMA acryl groups sensitive to temperature.

In addition, the polymerization inhibitor serves to terminate a reaction by inhibiting an exothermic reaction occurring locally in the late polymerization and removing unreacted residual radicals, and may be one or more selected from the group consisting of hydroquinone (HQ), hydroquinone monomethyl ether, p-benzoquinone and phenothiazine, but the present invention is not particularly limited thereto.

Here, the step of synthesizing a shape-memory polymer may be performed at 80 to 140° C., or 100 to 130° C. on average. More specifically, when polymer synthesis is performed at less than 100° C., a catalytic reaction may not proceed, and when polymer synthesis is performed at more than 130° C., a catalytic reaction rate may be reduced.

Crosslinking is performed on the SMP. Crosslinking is a step for maintaining a SMP in a stable shape. Specifically, crosslinking may refer to chemical crosslinking, and in the crosslinked polymer, individual polymer chains are covalently bonded, so that the SMP may be maintained in a stable shape.

Crosslinking is for maintaining SMP in a stable shape, and may give an initial shape. That is, crosslinking may be performed when the initial shape is given, not in SMP synthesis. For example, when the vascular anastomotic member is manufactured, a SMP may be poured in a mold after being dissolved, and during the SMP dissolution, a crosslinking agent may be added, and a crosslinking reaction may be induced.

Particularly, a melting temperature may be further reduced by inducing a photo-crosslinking reaction in the synthesized shape-memory polymer, and for example, crosslinking is induced by ultraviolet (UV) irradiation at 320 to 500 nm, and the melting temperature of the shape-memory polymer may be reduced to 28 to 42° C. For example, 320 to 500-nm UV irradiation may be applied to the shape-memory polymer of Formula 1, and in this case, a methacrylate group, which is a functional group included in Formula 1, may react with a methacrylate group of another chain, thereby forming a covalent bond.

Further, in one embodiment of the present invention,
a vascular anastomotic member including the above-described SMP is provided.

As an example, the vascular anastomotic member may be in the form of a tube inserted into an end of a first blood vessel or second blood vessel.

Here, the vascular anastomotic member may be in the form of a tube, and consist of a SMP, so that the shape of the member may be changed according to inner diameters of the first blood vessel and the second blood vessel at an average temperature of 28 to 42° C. or more. The tubular vascular anastomotic member may be applied to suturing and anastomosis of blood vessels, and in the case of anastomosis, it may be applied in end-to-end anastomosis.

As another example, the vascular anastomotic member may be a type of vascular anastomotic member that surrounds a damaged site of a blood vessel.

Here, the vascular anastomotic member may have a sheet shape and consist of a SMP, so that the shape of the member may be changed to surround the outer diameter of a blood vessel at an average temperature of 28 to 42° C. or more. In addition, the vascular anastomotic member according to the present invention may be applied in suturing and anastomosis of blood vessels, and in the case of anastomosis, it may be applied to both of end-to-end anastomosis and end-to-side anastomosis.

Meanwhile, the vascular anastomotic member according to one embodiment of the present invention may be a biodegradable SMP.

More specifically, the "biodegradable SMP" is, as described above, a polymer material which is decomposed and absorbed in the human body over time, and whose shape is changed according to a temperature change, and a polymer whose shape can be changed according to a temperature change, and decomposed and absorbed in the human body.

Particularly, since the vascular anastomotic member consists of a biodegradable SMP, it is possible to minimize various causes that can adversely affect blood flow according to a physical change of a blood vessel through an external change of the SMP, rather than the physical change of a human blood vessel, and when a patient in a growth period undergoes a procedure with an artificial blood vessel consisting of a material semi-permanently remaining in the human body, the growth of a blood vessel may be suppressed so that a problem of repetitive vascular procedures after a certain period of time can be solved.

In addition, when the above-described vascular anastomotic member including a biodegradable SMP is applied to a damaged site of a blood vessel, a new blood vessel wall may be regenerated at the damaged site of the blood vessel by growing endothelial cells without inflammation or a foreign body reaction, and serve as a blocking layer that blocks blood vessels during regeneration of a block vessel wall so as not to disturb the regeneration from an external environment, and effectively heal the blood vessel by improving the biodegradability of the vascular anastomotic member and the regeneration effect of the damaged site of the blood vessel.

Meanwhile, the vascular anastomotic member may have a perforation in one area, and a branch tube may be integrally connected to the area corresponding to the perforation. Here, the perforation is formed to correspond the inner diameter of the branch tube, and the branch tube may communicate with the damaged site of the blood vessel. For reference, this is applied to end-to-side anastomosis, and the branch tube may be connected with one end of a blood vessel, and a sheet-shape vascular anastomotic member may be connected with a side of a blood vessel. A more detailed description will be described below.

In addition, in the branch tube is connected with an end of one blood vessel as described above, guide protrusions may be formed on the inner circumference surface to be extended in a longitudinal direction of the axis of the branch tube. Here, the branch tube may include one or more types of biocompatible polymers selected from the group consisting of polyethylene glycol, polyglycolide, poly-L-lactide, poly-D,L-lactide, poly(lactide-co-glycolide) and hyaluronic acid.

In addition, the present invention provides a method of manufacturing an artificial blood vessel or vascular anastomotic member, which includes a SMP. For example, the artificial blood vessel or vascular anastomotic member may be formed in a tubular shape using a blood vessel-shaped mold. More specifically, the artificial blood vessel or vascular anastomotic member may be manufactured by preparing a reactant by dissolving a SMP and an initiator in a solvent, pouring the reactant in a tubular mold, and performing crosslinking. The mold may be glass or a PDMS material, and is for improving light transmission for crosslinking.

Here, the diameter of the mold may be determined according to the inner diameter of a blood vessel to be applied, and as an example, an inner wall mold may have an outer diameter of 2 mm and a length of 10 mm or more. Moreover, when an outer wall mold has an inner diameter of 2.2 mm or less, the thickness of the manufactured vascular anastomotic member may be maintained at 100 to 200 μm.

Meanwhile, a temperature in the crosslinking process may be room temperature. For example, crosslinking may be performed at 15 to 25° C., 17 to 23° C., 19 to 21° C., or 20° C. When the reaction temperature exceeds the above-mentioned temperature, due to the generation of air bubbles, an unexpected porous structure may be formed in the manufactured vascular anastomotic member, and therefore, to reduce a temperature, a chiller may be used.

A solvent used herein may be one or more selected from the group consisting of diethyl ether, chloroform, 1,4-dioxane, dichloromethane, ethyl acetate, tetrahydrofuran, acetone, acetonitrile, N,N-dimethylformamide, N,N-dimethylacetamide, N-methylpyrrolidone, dimethyl sulfoxide, acetonitrile, methyl ethyl ketone, and diethyl ketone.

The initiator may be a photo-initiator, which may form a radical by UV irradiation, and may be selected from the group consisting of 2,2-dimethoxy-2-phenylacetonephenone (DMPA), 2-hydroxy-2-methylpropipphenone (HOMPP), lithium phenyl-2,4,6-trimethylbenzoylphosphinate (LAP), and 1-[4-(2-hydroxyethoxy)-phenyl]-2-hydroxy-2-methyl-1-propane-1-one (IRGACURE 2959), which may be used in an aqueous solution, but the present invention is not limited thereto. The initiator may be included at 0.1 to 0.5 w/v %, 0.2 to 0.4 w/v %, or 0.3 w/v % with respect to a solvent. When the concentration of the photo-initiator is too low, a photo-polymerization reaction may not effectively progress, and when the concentration of the photo-initiator is too high, the loss of SMP characteristics may be observed.

Moreover, a SMP may be included at 30 to 300 w/v %, 30 to 270 w/v %, 35 to 240 w/v %, 40 to 210 w/v %, 45 to 170 w/v %, 50 to 140 w/v %, 50 to 100 w/v %, 65 to 90 w/v %, or 75 w/v % with respect to the solvent.

For example, according to processes of shape change of a tubular vascular anastomotic member and vascular anastomosis, when an original shape of vascular anastomotic member is elongated by applying a physical force to both sides at a melting temperature or less, the vascular anastomotic member is stretched in a longitudinal direction, thereby reducing the outer diameter thereof, and then changed into a temporary shape to be inserted into a blood vessel through a cut section of a blood vessel to be anastomosed.

Here, when a temperature of the vascular anastomotic member is reduced to 0° C. or less while the shape of the vascular anastomotic member is maintained in a temporary shape, the vascular anastomotic member is fixed in the temporary shape, and when heated to a transition temperature or more (approximately 28 to 42° C.), the vascular anastomotic member is restored to the initial shape before a shape change by a physical force so that a permanent shape may be maintained. That is, the vascular anastomotic member is contracted in a longitudinal direction in the cut blood vessel, thereby increasing the outer diameter thereof, and the outer circumference surface of the body 100 may be fixed in the permanent shape in a state of being brought into close contact with the inside of the cut blood vessel, resulting in vascular anastomosis.

For a SMP, the "strain" refers to a rate indicating how much a shape changes when a SMP is restored to an initial shape from a temporary shape and thus maintained in a permanent shape, and a rate of changing from a temporary shape to a permanent shape. In addition, the "strain recovery rate" refers to a recovery rate when a SMP is restored to the initial original shape before being changed from the temporary shape by a physical force, and a ratio of the initial shape and the permanent shape. The strain in the present invention may be changed by a ratio or condition (temperature, UV, etc.) of a monomer included in a SMP, and specifically, 5 to 350%. In addition, the strain recovery rate may be 90% or more.

Hereinafter, the present invention will be described in detail with reference to the following embodiments. The following examples are merely provided to exemplify the present invention, and the contents of the present invention are not limited to the following embodiments.

Figure 2:
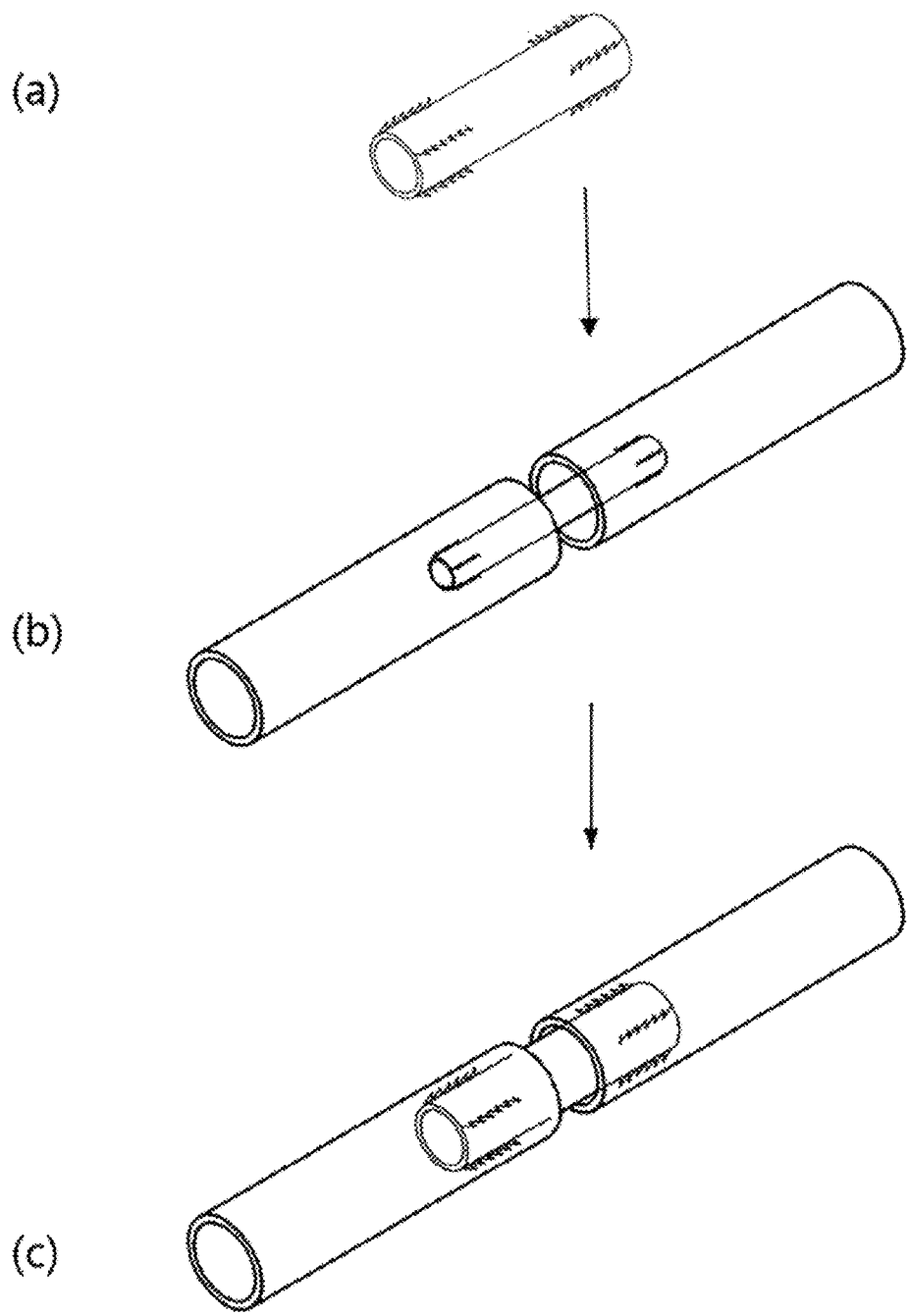
FIG. 2 shows a process of the morphological change in a vascular anastomotic member according to the present invention ((a) initial shape, (b) temporary shape (deformed state), (c) permanent shape (recovered state)).

FIG. 1 shows a process of the morphological change in a vascular anastomotic member according to the present invention, and FIG. 2 shows a process of the morphological change in a vascular anastomotic member according to the present invention ((a) initial shape, (b) temporary shape (deformed state), (c) permanent shape (recovered state)).

Referring to FIGS. 1 and 2, the vascular anastomotic member 100 of the present invention is a SMP which is inserted into a first blood vessel and a second blood vessel of a blood vessel and whose shape is changed according to the inner diameter of the blood vessel.

As such, the vascular anastomotic member 100 according to one embodiment of the present invention offers s a structure which connects two blood vessels by changing its shape according to the shape of the inner diameter applied inside the blood vessel, and therefore, such vascular anastomosis can be much simpler and more convenient than conventional anastomosis with a suture, reduce the time for a vascular anastomosis procedure, and improve surgical stability by reducing errors that may occur during the anastomosis procedure.

Further, the vascular anastomotic member according to the present invention may be changed in shape according to the inner diameters of a first blood vessel and a second blood vessel at 28 to 42° C. or more on average. In one example, at less than 28° C., the vascular anastomotic member may have a smaller inner diameter than the blood vessel to be anastomosed, and at 28 to 42° C. or more on average, may be changed according to the shape and size of the inner diameter of the blood vessel.

More specifically, the vascular anastomotic member is formed of a SMP of Formula 1, and restored to an initial shape before change by a physical force at 28 to 42° C. or more. Therefore, as it is fixed to the inner diameter of the blood vessel to be anastomosed, two cut blood vessels may be anastomized. Here, the physical force may refer to an external stimulus applied to change the vascular anastomotic member from the initial shape to the temporary shape, and it may be a stimulus such as a temperature or light, or a mechanical force at a melting temperature or less.

Meanwhile, the forming of the vascular anastomotic member to be restored to the initial shape at 28 to 42° C. or more is to induce a spontaneous shape change in the human body during a procedure with the vascular anastomotic member of the present invention. That is, this is for securing a spontaneous shape change at a body temperature of approximately 36 to 38° C.

In addition, the vascular anastomotic member 100 of the present invention may have a tubular shape which is easily inserted into the first blood vessel and the second blood vessel, and fixing protrusions on its outer circumference surface to be easily fixed to a blood vessel.

The fixing protrusions may be a plurality of microneedles which penetrate into the inner vascular wall when the vascular anastomotic member 100 is inserted into the blood vessel to allow the vascular anastomotic member to be firmly fixed to the inside of the blood vessel. Meanwhile, the fixing protrusion may consist of a biodegradable polymer which is decomposed over time and absorbed in the human body.

The length of the vascular anastomotic member according to the present invention may be 5 to 20 mm, 7 to 18 mm, 9 to 16 mm, or 11 to 14 mm. In addition, the inner diameter of the vascular anastomotic member may be 0.1 to 4 mm before transplantation into the blood vessel, and 0.2 to 5 mm after transplantation. However, according to the content of a SMP included in the vascular anastomotic member or a crosslinking condition, the temporary shape before transplantation may have a larger diameter than the permanent shape after transplantation, but in the present invention, the vascular anastomotic member may be designed to have a smaller diameter before transplantation to be easily inserted into the blood vessel during surgery.

Specifically, in the case of the temporary shape before transplantation, the vascular anastomotic member may have an inner diameter of 0.1 to 4 mm, 0.5 to 3.5 mm, 0.7 to 3.0 mm, 0.9 to 2.5 mm, 1.1 to 2.0 mm, or 1.5 mm, and in the case of the permanent shape after transplantation, the vascular anastomotic member may have an inner diameter of 0.2 to 5 mm, 0.5 to 4 mm, 0.7 to 3.5 mm, or 1.0 to 3 mm. Meanwhile, the diameter of the vascular anastomotic member may vary according to a blood vessel and site to be anastomosed.

In one example, the inner diameter of the vascular anastomotic member may be 2 mm before transplantation into the blood vessel, and 4 mm after transplantation. The degree of change may be adjusted by controlling the composition of the polymer, a crosslinking time, and UV energy during crosslinking.

Further, the inner diameter of the vascular anastomotic member according to the present invention may be 0.2 to 5 mm, and the inside of the vascular anastomotic member may have a flare shape with a diameter that gradually increases from the first direction to the second direction. Here, the "first direction" and "second direction" may refer to directions of the blood flow. More specifically, the "first direction to the second direction" describes a direction of the blood flow from the first blood vessel to the second blood vessel.

Meanwhile, the sectional thickness of the vascular anastomotic member may be 50 to 200 μm, preferably, 100 to 200 μm, or 100 μm. More preferably, the inner diameters and step differences of the first blood vessel and the second blood vessel into which the vascular anastomotic member is inserted may be reduced by determining the sectional thickness of the vascular anastomotic member within the above-mentioned range, resulting in a reduction in the vortex phenomenon of a fluid (blood). That is, the thickness of the vascular anastomotic member is for inhibiting the generation of a blood flow vortex and maintaining mechanical strength, and this may be a result obtained through computational modeling and an experiment to minimize the step difference of the thickness of an artificial blood vessel or anastomizer when blood flows into a target blood vessel.

In one example, when the inner diameters of the ends of the first blood vessel and the second blood vessel are 2.0 mm, the inner diameter of the vascular anastomotic member may be 1.8 or 1.9 mm. When the step difference in inner diameter between the vascular anastomotic member and the blood vessel is small, the vortex phenomenon of a fluid may be reduced.

Meanwhile, the vascular anastomotic member may include an antithrombotic material, or fixed on the surface thereof, so that it can prevent problems such as blood coagulation and blood clots that may occur when contacting the blood in the blood vessel.

The anti-thrombotic material may be heparin, a mixture of heparin and a CD 133 antibody or a functional peptide releasing nitric oxide (NO), and for example, heparin.

Further, in the manufacturing of the vascular anastomotic member, by adjusting a ratio of the weight of a SMP with respect to the volume of the solvent, the strength (Young's modulus), a crosslinking degree and a melting temperature of the vascular anastomotic member may be adjusted.

Specifically, the strength of a SMP may be confirmed by measuring the Young's modulus, and the Young's modulus of a SMP may be 0.01 to 200 MPa, 0.1 to 150 MPa, or 0.1 to 120 MPa. For example, the average Young's modulus of the blood vessel is 15 N/mm$^2$, and the average Young's modulus of a microvessel having endothelial cells as a main component is approximately 2-3 N/mm$^2$. The average Young's modulus of an arteriole or vein may fall to 0.5 N/mm², and the average Young's moduli of blood vessels with a thick muscle layer or highly-accumulated fats may be 100 N/mm² or more. Therefore, the vascular anastomotic member of the present invention exhibits a property of covering all of the physical strength ranges of the blood vessel by controlling the components of a SMP and the wt % of each component.

Figure 3:
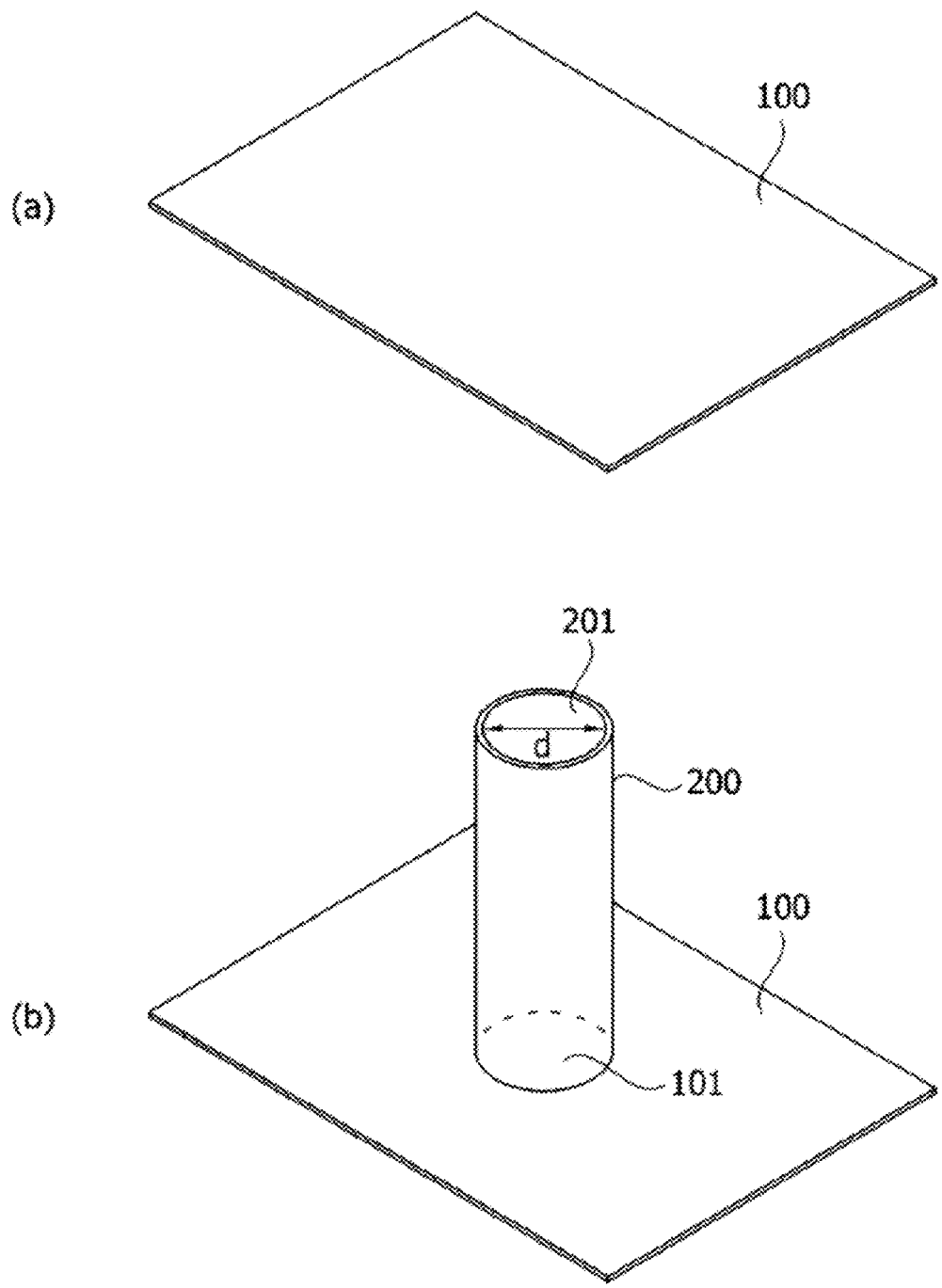
FIG. 3 shows a vascular anastomotic member of the present invention ((a) end-to-end vascular anastomotic member, (b) end-to-side vascular anastomotic member).

FIG. 3 shows a vascular anastomotic member of the present invention, and FIG. 3A shows an end-to-end vascular anastomotic member.

Referring to FIG. 3A, the vascular anastomotic member 100 of the present invention may be a SMP which has a sheet shape disposed to surround the outer circumference surface of a damaged site of a blood vessel and whose shape is changed according to the outer diameter of the blood vessel.

As such, the vascular anastomotic member 100 according to one embodiment of the present invention offers a structure which is formed to surround the outer circumference surface of a blood vessel, and connects one or two blood vessels for vascular anastomosis, and therefore, such vascular anastomosis can be much simpler and more convenient than conventional anastomosis with a suture, reduce the time for a vascular anastomosis procedure, and improve surgical stability by reducing errors that may occur during the anastomosis procedure.

Particularly, the vascular anastomotic member of the present invention may be formed to surround the outer circumference surface of a blood vessel to be anastomosed, rather than being inserted into the blood vessel to support the blood vessel, and thus the blood flow in the blood vessel may smoothly flow, and problems that may occur while contacting blood in the blood vessel may be minimized.

Further the vascular anastomotic member is changed in shape to surround the outer diameter of the blood vessel at 28 to 42° C. or more on average.

More specifically, the vascular anastomotic member consists of a SMP, and may be fixed to surround the outer surface of the blood vessel by recovering its initial shape before a shape change by a mechanical force at 28 to 42° C. or more to suture one blood vessel or anastomize two cut blood vessels.

Meanwhile, the forming of the vascular anastomotic member to be restored to an initial shape at 28 to 42° C. or more is to induce a spontaneous shape change in the human body during a procedure with the vascular anastomotic member of the present invention. That is, this is for securing a spontaneous shape change at a body temperature of approximately 36 to 37° C.

For reference, FIG. 3A shows a flat sheet shape, which is provided to describe the present invention, not to limit the present invention. As an example, the flat sheet shape in the drawing represents a shape after a shape change at an external temperature of 28 to 42° C. or more, and it may be a shape that surrounds a blood vessel in an initial deformed shape at 28 to 42° C. or more.

FIG. 3B shows an end-to-side vascular anastomotic member.

Referring to FIG. 3B, the vascular anastomotic member 100 of the present invention may have a perforation 101 in one area, and a branch tube 200 may be integrally connected to the area corresponding to the perforation 101.

Here, the "branch tube" is a tube growing from a main tube, and may refer to a tube diverging from the vascular anastomotic member 100 when an artificial blood vessel is formed through vascular anastomosis by surrounding a blood vessel with the vascular anastomotic member 100.

For reference, when the vascular anastomotic member is formed to surround one blood vessel (first blood vessel), the branch tube may be connected with an end of another blood vessel (second blood vessel).

Further, the perforation 101 and the inner diameter 201 of the branch tube 200 may communicate to correspond to each other, and the branch tube 200 may communicate with a damaged site of the blood vessel.

In addition, the branch tube may consist of one or more types of biocompatible polymers selected from the group consisting of polyethylene glycol, polyglycolide, poly-L-lactide, poly-D,L-lactide, poly(lactide-co-glycolide) and hyaluronic acid.

Figure 4:
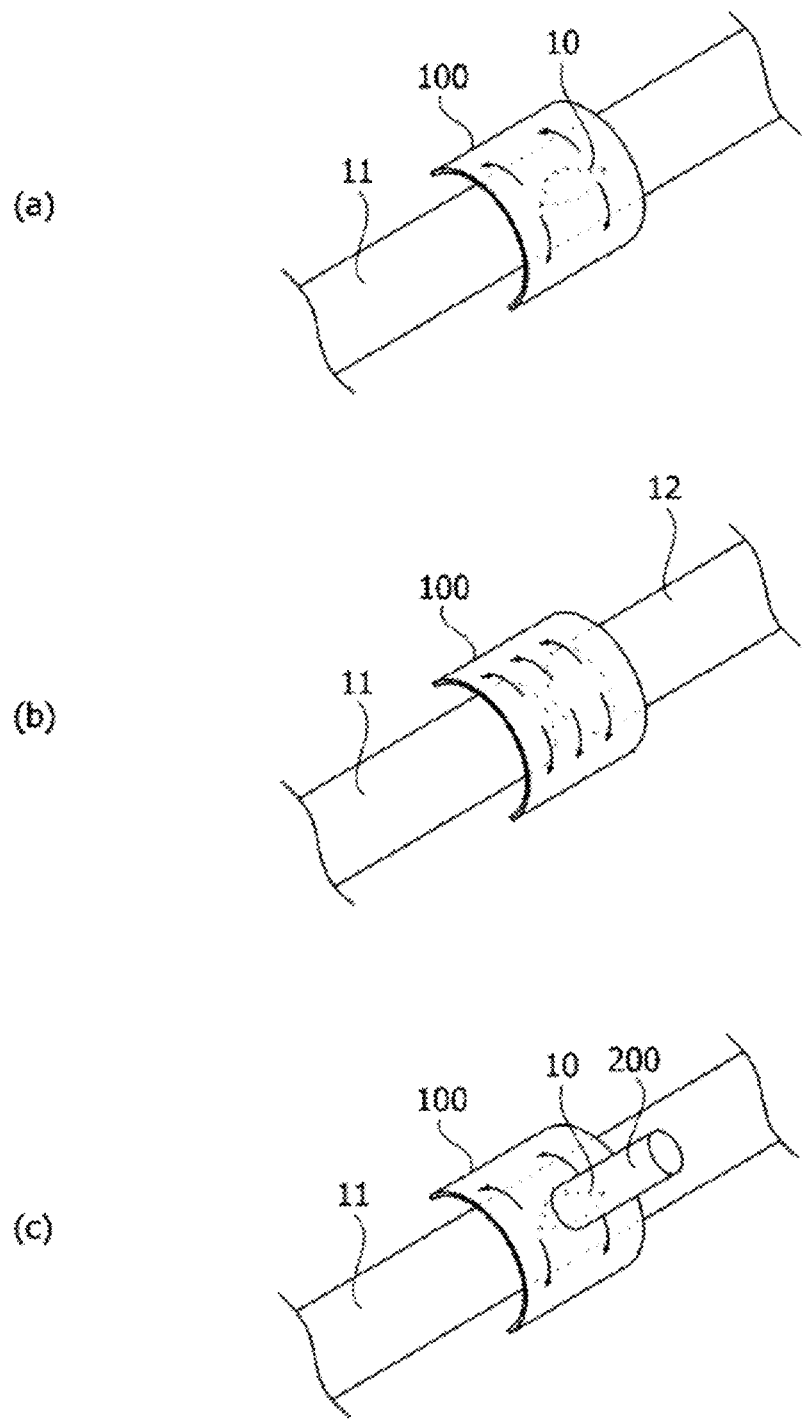
FIG. 4 shows various forms of a vascular anastomotic member of the present invention ((a) for vascular anastomosis, (b) for end-to-end vascular anastomosis, (c) end-to-side vascular anastomosis).

FIG. 4 shows various forms of a vascular anastomotic member according to one embodiment of the present invention.

More specifically, FIG. 4A shows a sheet-shaped vascular anastomotic member 100 of the present invention manufactured for suturing blood vessels, which may be formed to suture a blood vessel 11 to cover a damaged site 10 thereof.

FIG. 4B shows a vascular anastomotic member 100 of the present invention manufactured for end-to-end vascular anastomosis.

More specifically, the end-to-end vascular anastomosis is to interlock an end of the first blood vessel 11 and an end of the second blood vessel 12, and it may refer to an anastomotic procedure for connecting broken vessels to be one when the blood vessels, which were originally connected, are disconnected.

FIG. 4C shows a vascular anastomotic member 100 of the present invention manufactured for end-to-side vascular anastomosis.

That is, anastomosis may be performed to interlock a side 11 of a first blood vessel and an end of a second blood vessel (not shown).

Figure 5:
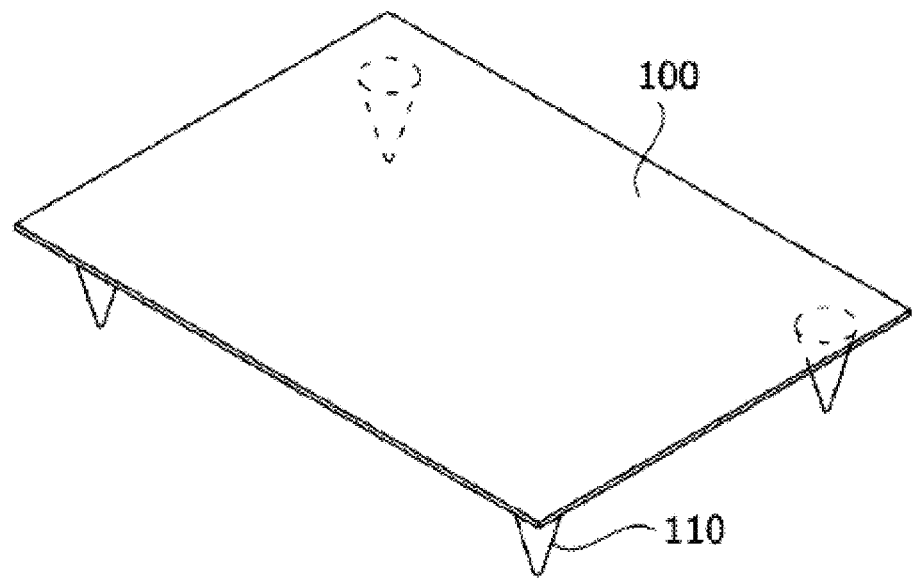
FIG. 5 shows the structure of a vascular anastomotic member of the present invention.

FIG. 5 shows the structure of a vascular anastomotic member according to one embodiment of the present invention.

The vascular anastomotic member 100 according to one embodiment of the present invention may include a plurality of fixing protrusions 110 to be easily applied to a damaged blood vessel. More specifically, the plurality of protrusions 110 may project from the back side of the vascular anastomotic member 110 such that the vascular anastomotic member is easily fixed when applied to surround the blood vessel.

For reference, the plurality of protrusions 110 may include at least two protrusions, and may be applied to suturing or end-to-side anastomosis of a blood vessel.

More specifically, the plurality of protrusions may contact each other when the vascular anastomotic member 100 surrounds a damaged site of the blood vessel, and the two protrusions 110 may be formed at each side of the vascular anastomotic member, which may meet each other.

In another aspect, the plurality of protrusions 110 may be formed at edges of the vascular anastomotic member 100 in the drawing, and may be applied to end-to-end anastomosis. Specifically, the plurality of protrusions 110 may be formed at edges of the vascular anastomotic member so as to be fixed to each of the first blood vessel 11 and the second blood vessel 12 connected to each other.

Meanwhile, the plurality of protrusions 110 may have a predetermined angle.

More specifically, the protrusions may have an angle of 90° with the vascular anastomotic member, and when applied to end-to-end anastomosis, the plurality of protrusions 110 is preferably formed to have an acute angle facing the center of the vascular anastomotic member 100. Here, the angle may be 45 to 85° or 60 to 75°.

This is to tightly embed the vascular anastomotic member 100 in a damaged site of a blood vessel and thus prevent it from falling out easily, and the angle may vary depending on a case when needed.

Figure 6:
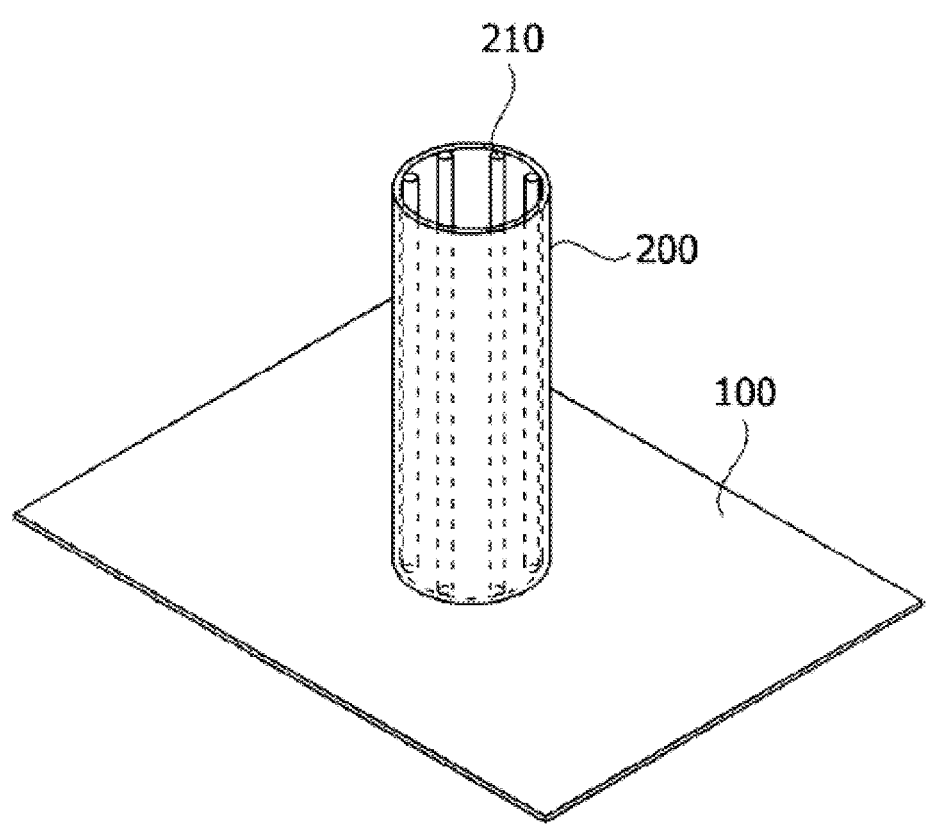
FIG. 6 shows the structure of a vascular anastomotic member of the present invention.

FIG. 6 shows the structure of a vascular anastomotic member according to one embodiment of the present invention.

Referring to FIG. 6, the branch tube 200 according to one embodiment of the present invention may have guide protrusions 210 on the inner circumference surface thereof.

The guide protrusion 210 may guide the direction of the blood flow flowing through the branch tube 200, and protrusions may be formed to extend in the longitudinal direction along the axis of the branch tube 200. A plurality of the guide protrusions 210 may be formed as needed according to a conventional pattern forming method used in tissue engineering.

In addition, the branch tube may be a cylindrical branch tube 200 with a constant diameter, or a flare-shaped branched blood vessel whose diameter increases towards a part connected to the vascular anastomotic member, but the present invention is not limited thereto. For reference, to facilitate blood flow in the artificial blood vessel, a flare-shaped branch blood vessel member may be used.

For reference, when the branch tube is applied to arteries with a wide diameter, such as the carotid artery, the length of the vascular anastomotic member may be 15 to 30 mm, and the length of the branch tube 200 may be 3 to 15 mm, but the present invention is not limited thereto.

Examples of the use of the vascular anastomotic member of the present invention configured as described above will be briefly described with reference to FIGS. 5 and 6 as follows.

Figure 7:
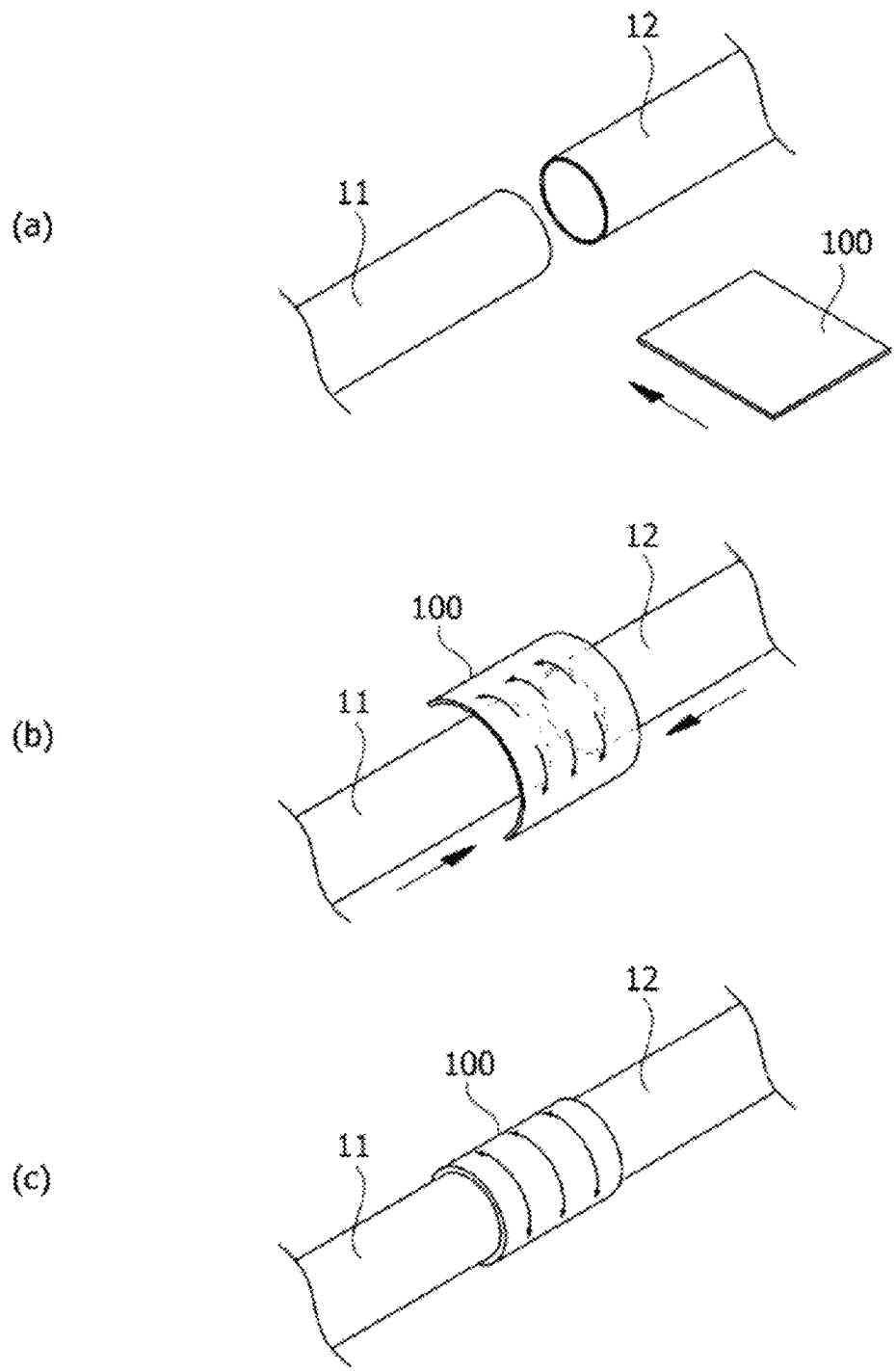
FIG. 7 is a schematic diagram of the process of vascular anastomosis (end-to-end) by applying a vascular anastomotic member according to one embodiment of the present invention to a damaged vascular site.

FIG. 7 is a schematic diagram of the process of vascular anastomosis (end-to-end) by applying a vascular anastomotic member according to one embodiment of the present invention to a damaged vascular site.

Referring to FIG. 7, in the process of vascular anastomosis, referring to FIG. 7A, the vascular anastomotic member 100 may be elongated by applying a mechanical force to both sides at room temperature (approximately 25° C.), which a transition temperature or less, to change it into a sheet-shaped temporary shape that is easy to apply to a blood vessel.

In addition, the cut first blood vessel 11 and second blood vessel 12 are moved to be joined to each other, and when the vascular anastomotic member 100 is slowly heated while being maintained in a temporary shape near the joined first blood vessel 11 and second blood vessel 12 (here, the temperature is increased up to approximately room temperature), the vascular anastomotic member 100 is fixed in a temporary shape (FIG. 7B). In addition, when heat is applied again so that a temperature becomes 37° C., which is a transition temperature or more, the vascular anastomotic member is restored to an initial original shape before a shape change by a mechanical force and maintained in a permanent shape as shown in FIG. 7C.

In this way, the vascular anastomotic member is permanently fixed to the damaged site of the blood vessel, resulting in end-to-end vascular anastomosis.

Figure 8:
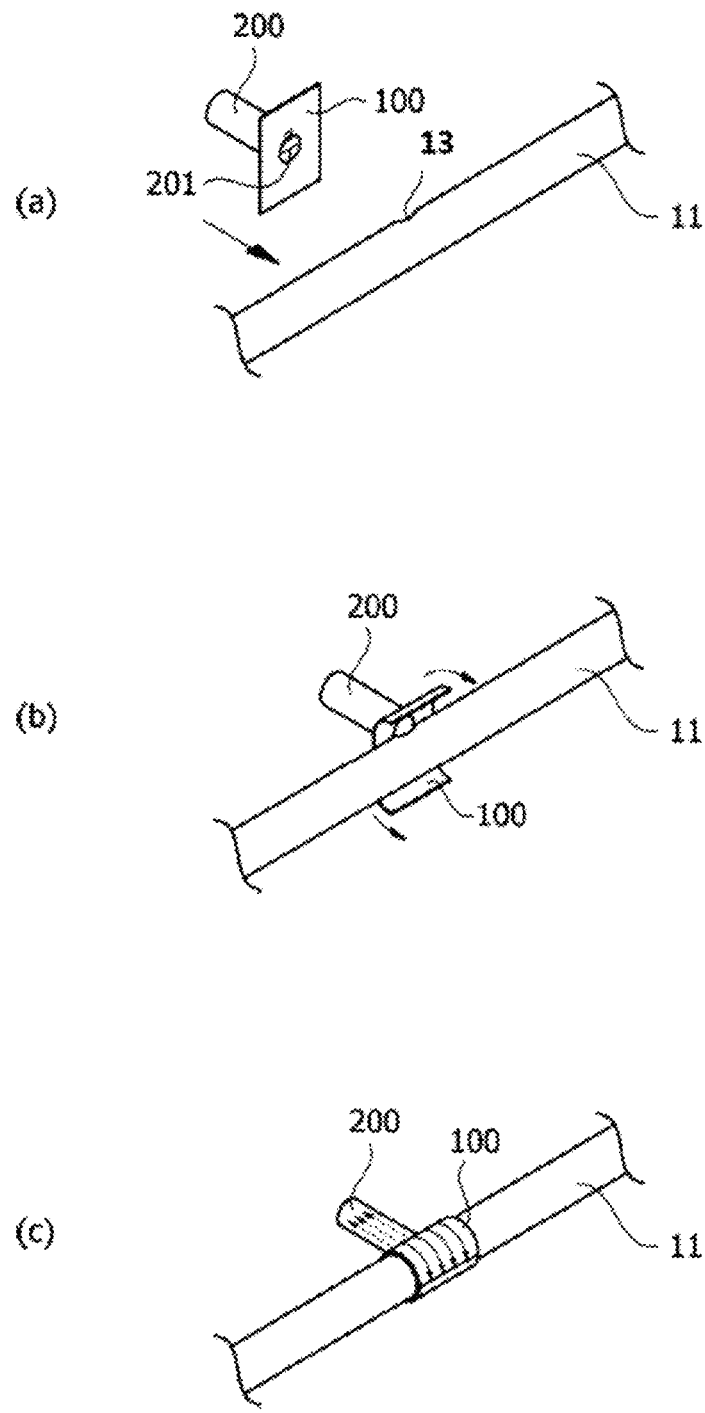
FIG. 8 is a schematic diagram of the process of vascular anastomosis (end-to-side) by applying a vascular anastomotic member according to another embodiment of the present invention to a damaged vascular site.

FIG. 8 is a schematic diagram of the process of vascular anastomosis (end-to-side) by applying a vascular anastomotic member according to another embodiment of the present invention to a damaged vascular site. Meanwhile, the damaged site of the blood vessel in the end-to-side vascular anastomosis may be damage to the blood vessel caused by an accident or error, but in another aspect, may refer to intentional vascular perforation to perform vascular anastomosis.

Accordingly, in the end-to-side vascular anastomosis, the "damaged site of a blood vessel" refers to a "vascular perforation."

Referring to FIG. 8, in the end-to-side vascular anastomosis, first, a blocking device (not shown) for blocking blood flow is installed at each of an inlet and an outlet of an area of a blood vessel 11 in which a vascular perforation 13 is made by medical personnel, and then a vascular perforation 13 is formed in a side wall of the blood vessel 11.

Subsequently, to apply the vascular anastomotic member 100 of the present invention to the site of the blood vessel 11 in which the vascular perforation 13 is made, first, the vascular anastomotic member 100 is elongated by a mechanical force at a transition temperature or less, for example, 25° C., and changed into a sheet-like temporary shape which is easy to apply to a blood vessel (FIG. 8A).

In addition, when the site of the blood vessel 11 in which the vascular perforation 13 is made is positioned to be connected with a perforation 201 of the vascular anastomotic member 100, and then slowly heated while maintained in a temporary shape (here, the temperature is increased up to approximately room temperature), the vascular anastomotic member 100 is fixed in a temporary shape (FIG. 8B).

Meanwhile, the branch tube 200 integrated with the perforation 201 may be connected to the site of the blood vessel 10 in which the vascular perforation 13 is made.

In addition, when heat is applied again to a transition temperature or more, for example, 37° C., the vascular anastomotic member is restored to an initial original shape before a shape change by a mechanical force, and maintained in a permanent shape as shown in FIG. 8C.

In this way, the vascular anastomotic member is permanently fixed to the damaged site of the blood vessel, resulting in end-to-side vascular anastomosis.

Hereinafter, examples and experimental examples of the present invention will be described in further detail.

However, the following examples and experimental examples merely exemplify the present invention, but the disclosure of the present invention is not limited to the following examples and experimental examples.

EXPERIMENTAL PREPARATION

1. Experimental Tools and Methods

ε-Caprolactone (CL), hydroquinone (HQ), 1,5,7-triazabicyclo[4.4.0]dec-5-ene (TBD), glycidyl methacrylate (GMA), acetonitrile, chloroform, dichloromethane, diethyl ether, 2,2-dimethoxy-2-phenylacetophenone and 1,6-hexanediol (HD) were purchased from Sigma-Aldrich.

Meanwhile, thermal characteristics such as a melting temperature ($T_m$), a crystallization temperature ($T_c$), a glass transition temperature ($T_g$), melting enthalpy ($\Delta H_m$) and crystallization enthalpy ($\Delta H_c$) were measured with a sample mass ranging from 5 to 10 mg in an aluminum pan using an instrument for differential scanning calorimetry (Discovery DSC25; TA Instruments). In addition, a heating rate was 10° C./min, and the thermal characteristics were measured once in a range from −80 to 150° C.

In addition, a molecular weight and PDI were measured using an instrument for gel permeation chromatography (GPC; Agilent Technologies 1200 series). A column used herein is a PLgel 5 µm Mixed-D column (300 mm, Ø=7.5 mm), a solvent used herein is tetrahydrofuran, and a flow rate was measured to be 1.0 mL/min.

Crystallinity (Xc) corresponding to each sample was calculated by the following equation:

$$X_c = \frac{\Delta H_c}{\Delta H_c^\circ} \times 100\%$$

Here, $\Delta H°_c$ (139.5 J·g$^{-1}$) is the enthalpy of 100% crystalline PCL.

Water contact angles were measured with 10 μl sessile drops of distilled water using a contact angle measurement system (OCA20, DataPhysics).

Mechanical properties were measured by analyzing stress-strain curves using a dynamic machinery analyzer (DMA, Discovery DMA850, TA Instruments Inc.) in a strain mode controlled at a strain rate of 2%·min$^{-1}$.

The rheological behavior of 94% PCL-6% PGMA was investigated by changing a polymer concentration to 100 to 250% (w/v) in chloroform, and determining a corresponding viscosity for 150 seconds at 20° C. using conical and plate-shaped equipment with a diameter of 4 cm and a cone angle of 1°, for example, an AR 2000 EX rheometer (TA Instruments Inc.).

A shear viscosity was measured in a flow mode having a shear rate of 0.01 to 350 s$^{-1}$. SMP degradation was performed by immersing the 94% PCL-6% PGMA film (round disc shape, radius=15.6 mm) in Dulbecco's phosphate-buffered saline (DPBS) while stirring at 37° C. for 28 days, and the percent cumulative loss % of a dry weight was calculated from the non-decomposition value.

Example 1. Synthesis of PCL-co-PGMA SMP 1-1. Synthesis of 96% PCL-co-4% PGMA

96% PCL-co-4% PGMA was synthesized with a reactant input ratio of [CL]$_0$/[GMA]$_0$/[HD]$_0$/[TBD]$_0$/[HQ]$_0$=94/6/0.6/1/0.5 as follows (see Table 1).

TABLE 1

| | CL (mmol) | GMA (mmol) | HQ (mmol) | TBD (mmol) | HD (mmol) |
|---|---|---|---|---|---|
| Example 1-1 | 94 | 6 | 0.6 | 1 | 0.5 |

First, CL (94 mmol, 10.41 ml), HD (0.5 mmol, 60 mg) and HQ (0.6 mmol, 66 mg) were added to a glass reactor (250 ml), and after 10 minutes, GMA (6 mmol, 0.8 ml) was injected into the glass reactor. In addition, when it was determined that a temperature in the glass reactor in which two monomers were mixed was thermally stabilized, as a catalyst for inducing co-ring opening polymerization of CL and GMA, TBD (1 mmol, 140 mg) was dissolved in 1 ml of acetonitrile, injected into the glass reactor, and stirred for 6 hours at 110° C. All the procedures were performed under high-purity nitrogen.

After the reaction, the reactants were dissolved in 15 ml of chloroform, and slowly dropped into diethyl ether (400 ml) to precipitate. Subsequently, the precipitate was filtered with filter paper, the solvent was removed using a rotary evaporator and dried under reduced pressure, thereby synthesizing a PCL-co-PGMA polymer.

1-2. Synthesis of 94% PCL-co-6% PGMA

94% PCL-co-6% PGMA was synthesized with a reactant input ratio of [CL]0/[GMA]0/[HD]0/[TBD]0/[HQ]0/=90/10/1/1/0.5 as follows (see Table 2).

TABLE 2

| | CL (mmol) | GMA (mmol) | HQ (mmol) | TBD (mmol) | HD (mmol) |
|---|---|---|---|---|---|
| Example 1-2 | 90 | 10 | 1 | 1 | 0.5 |

Hereinafter, a polymerization method is the same as described in Example 1-1. In addition, the composition of the synthesized polymer (a repeat unit ratio of PCL and PGMA through a ratio of the number of hydrogen atoms of PCL and PGMA) was measured using $^1$H NMR (nuclear magnetic resonance), and the measurement result is shown in FIG. 9A.

Referring to FIG. 9A, the repeat unit percentage (%) of the repeat unit ratio of the PCL and GMA (PCL:PGMA=15:1) was calculated through $^1$H NMR analysis based on the chemical structure of the synthetic polymer, and it was confirmed that the repeat unit ratio in Example 1-2 is 94% PCL-co-6% PGMA.

In addition, referring to FIG. 9B, as a result of confirming a molecular weight through GPC analysis for the 94% PCL-co-6% PGMA (1-HD 0.5 mmol, 2-HD 0.25 mmol) polymer, a target level of Mw 10 kDa or less was confirmed, which was expected to be easily adjusted by adjustment of an introduction amount of the initiator.

1-3. Synthesis of 92% PCL-co-8% PGMA

92% PCL-co-8% PGMA was synthesized with a reactant input ratio of [CL]$_0$/[GMA]$_0$/[HD]$_0$/[TBD]$_0$/[HQ]$_0$=86/14/1.4/1/0.5 as follows (see Table 3).

TABLE 3

| | CL (mmol) | GMA (mmol) | HQ (mmol) | TBD (mmol) | HD (mmol) |
|---|---|---|---|---|---|
| Example 1-3 | 86 | 14 | 1.4 | 1 | 0.5 |

Hereinafter, a polymerization method is the same as described in Example 1-1. In addition, the composition of the synthesized polymer (a repeat unit ratio of PCL and PGMA through a ratio of the number of hydrogen atoms of PCL and PGMA) was measured using $^1$H NMR (nuclear magnetic resonance), and the measurement result is shown in FIG. 10.

Figure 10:
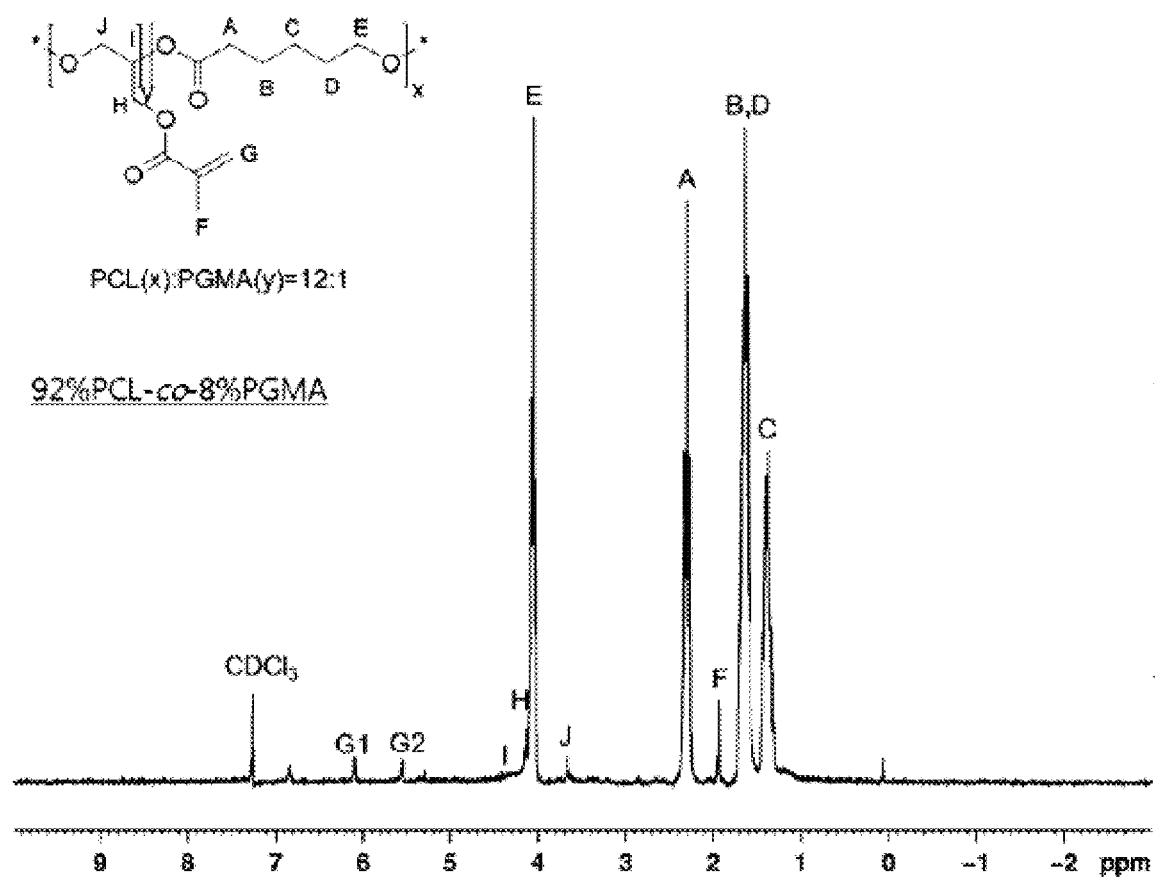
FIG. 10 shows the $^1$H NMR spectrum analysis result for a shape-memory polymer prepared in Example 1-3 of the present invention (92% PCL-co-8% PGMA).

Referring to FIG. 10, the repeat unit percentage (%) of the repeat unit ratio of the PCL and GMA (PCL:PGMA=12:1) was calculated through $^1$H NMR analysis, and it was confirmed that the repeat unit ratio of Example 1-3 is 92% PCL-co-8% PGMA.

1-4. Synthesis of 90% PCL-co-10% PGMA

90% PCL-co-10% PGMA was synthesized with a reactant input ratio of [CL]$_0$/[GMA]$_0$/[HD]$_0$/[TBD]$_0$/[HQ]$_0$=82/18/1.8/1/0.5 as follows (see Table 4).

TABLE 4

| | CL (mmol) | GMA (mmol) | HQ (mmol) | TBD (mmol) | HD (mmol) |
|---|---|---|---|---|---|
| Example 1-4 | 82 | 18 | 1.8 | 1 | 0.5 |

Figure 9:
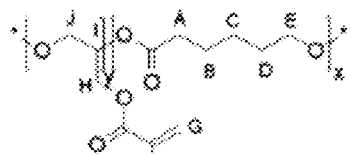
FIG. 9 show the $^1$H NMR spectrum and GPC analysis result for a shape-memory polymer prepared in Example 1-2 of the present invention (94% PCL-co-6% PGMA).
Figure 9:
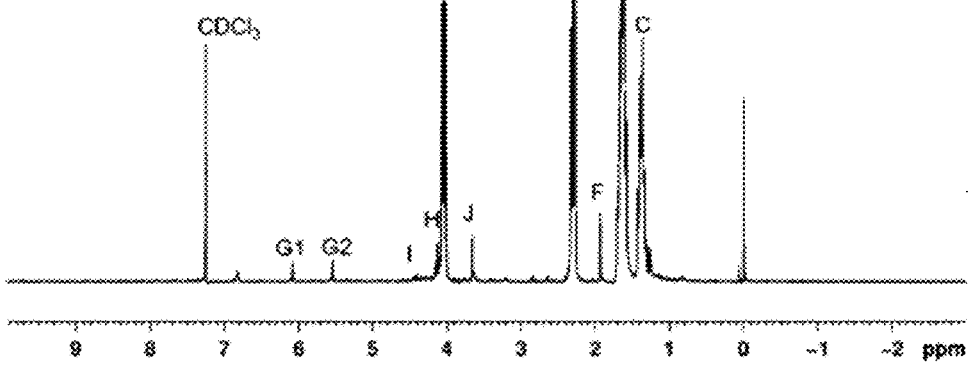
Figure 9:
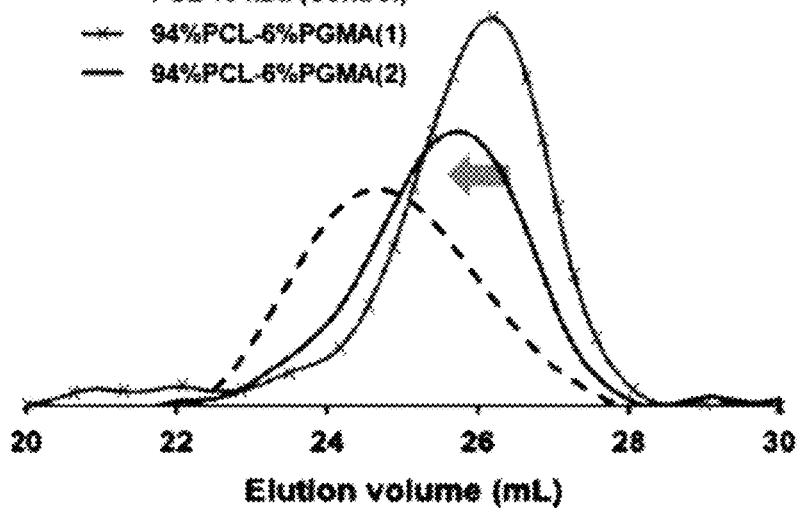

Hereinafter, a polymerization method is the same as described in Example 1-1. In addition, the composition of the synthesized polymer (a repeat unit ratio of PCL and PGMA through a ratio of the number of hydrogen atoms of PCL and PGMA) was measured using $^1$H NMR (nuclear magnetic resonance), and the measurement result is shown in FIG. 9.

Figure 11:
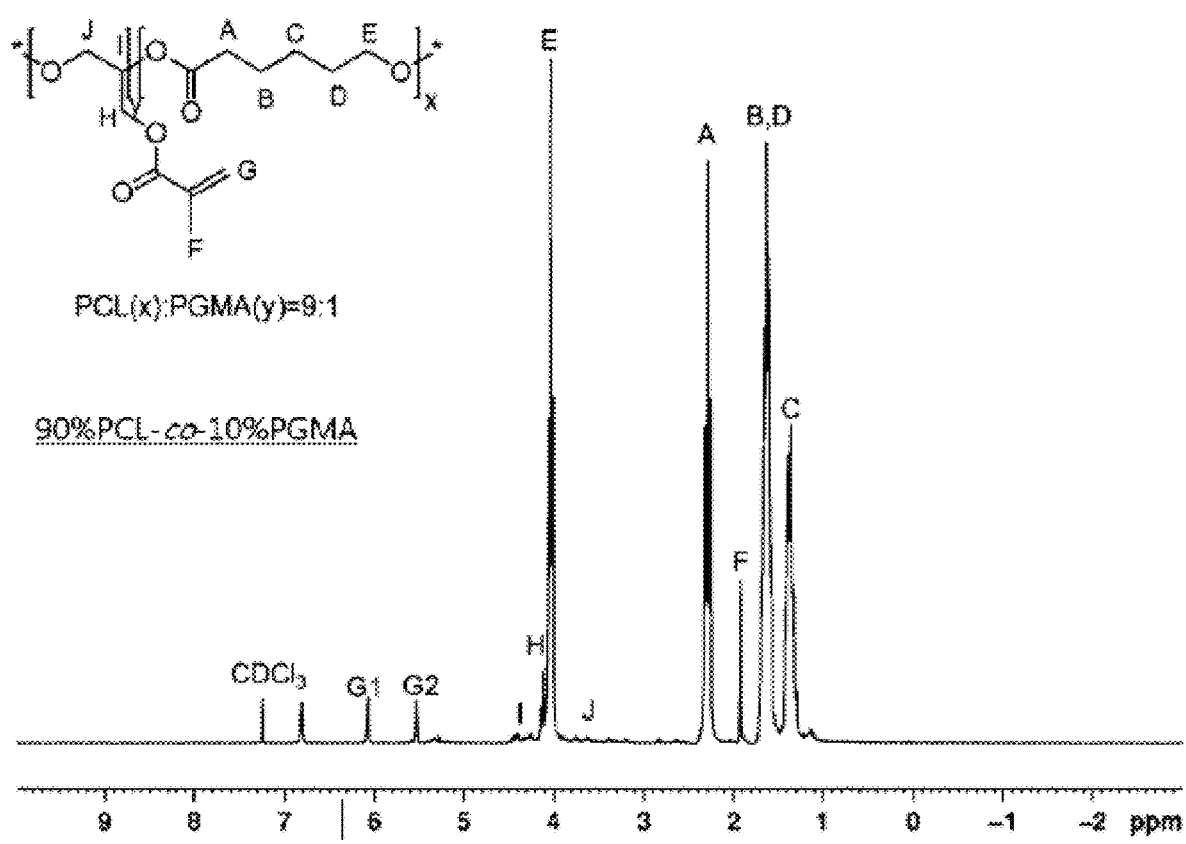
FIG. 11 shows the $^1$H NMR spectrum analysis result for a shape-memory polymer prepared in Example 1-4 of the present invention (90% PCL-co-10% PGMA).

Referring to FIG. 11, the repeat unit percentage (%) of the repeat unit ratio of the PCL and GMA (PCL:PGMA=9:1) was calculated through $^1$H NMR analysis, and it was confirmed that the repeat unit ratio of Example 1-4 is 90% PCL-co-10% PGMA.

1-5. Synthesis of 88% PCL-co-12% PGMA

88% PCL-co-12% PGMA was synthesized with a reactant input ratio of $[CL]_0/[GMA]_0/[HD]_0/[TBD]_0/[HQ]_0=78/22/2.2/1/0.5$ as follows (see Table 5).

TABLE 5

|  | CL (mmol) | GMA (mmol) | HQ (mmol) | TBD (mmol) | HD (mmol) |
|---|---|---|---|---|---|
| Example 1-5 | 78 | 22 | 2.2 | 1 | 0.5 |

Hereinafter, a polymerization method is the same as described in Example 1-1. In addition, the composition of the synthesized polymer (a repeat unit ratio of PCL and PGMA through a ratio of the number of hydrogen atoms of PCL and PGMA) was measured using $^1$H NMR (nuclear magnetic resonance), and the measurement result is shown in FIG. 12.

Figure 12:
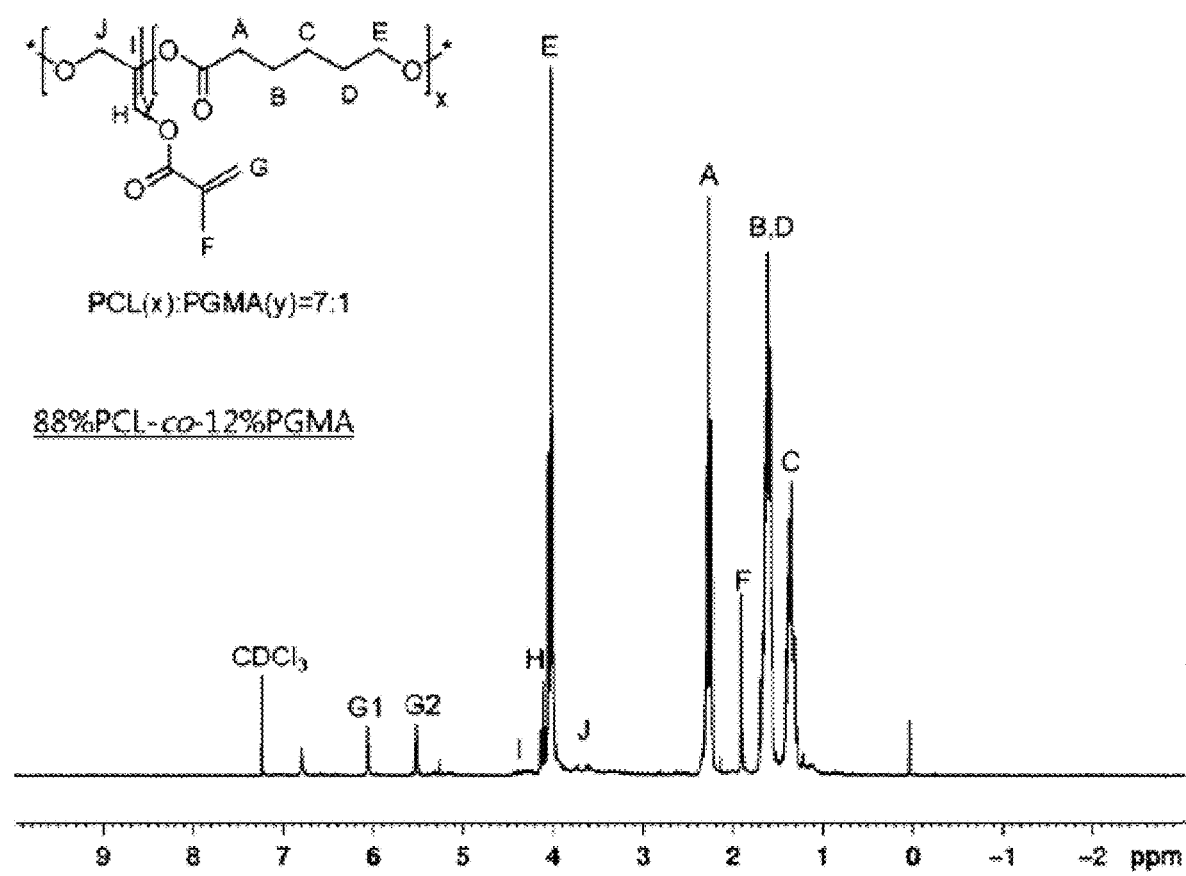
FIG. 12 shows the $^1$H NMR spectrum analysis result for a shape-memory polymer prepared in Example 1-5 of the present invention (88% PCL-co-12% PGMA).

Referring to FIG. 12, the repeat unit percentage (%) of the repeat unit ratio of the PCL and GMA (PCL:PGMA=7:1) was calculated through $^1$H NMR analysis, and it was confirmed that the repeat unit ratio of Example 1-5 is 88% PCL-co-12% PGMA.

Example 2. Synthesis of PCL-Co-PGMA SMP

A polymer was synthesized with a reactant input ratio of $[CL]_0/[GMA]_0/[HD]_0/[TBD]_0/[HQ]_0$ as follows (see Examples 2-1 to 2-5).

TABLE 6

|  | CL (mmol) | GMA (mmol) | HQ (mmol) | TBD (mmol) | HD (mmol) |
|---|---|---|---|---|---|
| Example 2-1 | 94 | 6 | 0.6 | 1 | 0.5 |
| Example 2-2 | 90 | 10 | 1 | 1 | 0.5 |
| Example 2-3 | 86 | 14 | 1.4 | 1 | 0.5 |
| Example 2-4 | 82 | 18 | 1.8 | 1 | 0.5 |
| Example 2-5 | 78 | 22 | 2.2 | 1 | 0.5 |

More specifically, in Examples 2-1 to 2-5, CL, HD and HQ were added to a glass reactor (250 ml). In addition, after 10 minutes, GMA (6 mmol, 0.8 ml) was injected into the glass reactor (see Table 6). In addition, when it was determined that a temperature in the glass reactor in which two monomers were mixed was thermally stabilized, as a catalyst for inducing co-ring opening polymerization of CL and GMA, TBD (1 mmol, 140 mg) was dissolved in 1 ml of acetonitrile, injected into the glass reactor, and stirred for 6 hours at 110° C. The following polymerization method is the same as described in Example 1-1.

In addition, a SMP that can be applied to the human body was prepared by irradiating the polymers synthesized in Examples 2-1 to 2-5 with UV light (250-500 nm) at an intensity of 265 mW/cm$^2$.

Example 3. Preparation of Graft Material for Vascular Anastomosis to Prevent Angiostenosis A graft material for vascular anastomosis was prepared using the polymer prepared in Example 1.

To prepare a tubular graft material for vascular anastomosis, a tubular mold was prepared, and to increase light transmittance for polymer crosslinking, inner/outer wall molds consisting of PDMS were prepared. Here, the outer diameter of the inner wall mold was 2 mm, and the length thereof was 10 mm. In addition, the inner diameter of the outer wall mold was 2.2 mm, and the length thereof was the same as that of the inner wall mold. Accordingly, the sectional thickness of the graft material for vascular anastomosis may be maintained to be 100 to 200 µm. In addition, a mold was formed by inserting the inner wall mold into the outer wall mold to create a space between them.

Afterward, the polymer prepared in Example 1 was poured in the space between the inner wall mold and the outer wall mold with respect to 10 g of a THF solvent, and crosslinking was performed in a UV crosslinker. Specifically, the polymer in the mold was irradiated with UV light (365 nm) at an intensity of 265 mW/cm$^2$, thereby preparing a graft material for vascular anastomosis.

Comparative Example 1. Poly(ε-Caprolactone) (PCL) Polymerization

Polymerization was performed with a reactant input ratio of $[CL]_0/[HD]_0/[TBD]_0=100/0.5/1$ as follows.

CL (100 mmol, 9.97 ml) and HD (0.5 mmol, 60 mg) were put into and mixed in a glass reactor (250 ml) (see Table 7).

TABLE 7

|  | HD (mmol) | TBD (mmol) | HQ (mmol) | CL (mmol) | GMA (mmol) |
|---|---|---|---|---|---|
| Comparative Example 1 | 0.5 | 1 | — | 100 | — |

When it was determined that a temperature in the glass reactor in which two monomers were mixed was thermally stabilized, as a solvent for inducing ring-opening polymerization of CL, TBD (1 mmol, 140 mg) was dissolved in 1 ml of acetonitrile, added to a glass reactor, and then stirred for 30 minutes at 110° C. The following polymerization method is the same as described in Example 1-1.

Comparative Example 2. PCL Polymerization-2

Polymerization was performed with a reactant input ratio of $[CL]_0/[HD]_0/[TBD]_0=100/0.5/0.5$.

CL (100 mmol, 9.97 ml) and HD (0.5 mmol, 60 mg) were added to and mixed in a glass reactor (250 ml) (see Table 8).

TABLE 8

|  | HD (mmol) | TBD (mmol) | HQ (mmol) | CL (mmol) | GMA (mmol) |
|---|---|---|---|---|---|
| Comparative Example 2 | 0.5 | 0.5 | — | 100 | — |

In addition, when it was determined that a temperature in the glass reactor in which monomers were mixed was thermally stabilized, as a solvent for inducing ring-opening polymerization of CL, TBD (0.5 mmol, 70 mg) was dissolved in 1 ml of acetonitrile, added to a glass reactor, and then stirred for 30 minutes at 110° C. The following polymerization method is the same as described in Example 1.

Experimental Example 1. Analysis of Characteristics of SMPs Prepared in Examples 1 and 2

1-1. Preparation of SMP by UV Crosslinking

Figure 13:
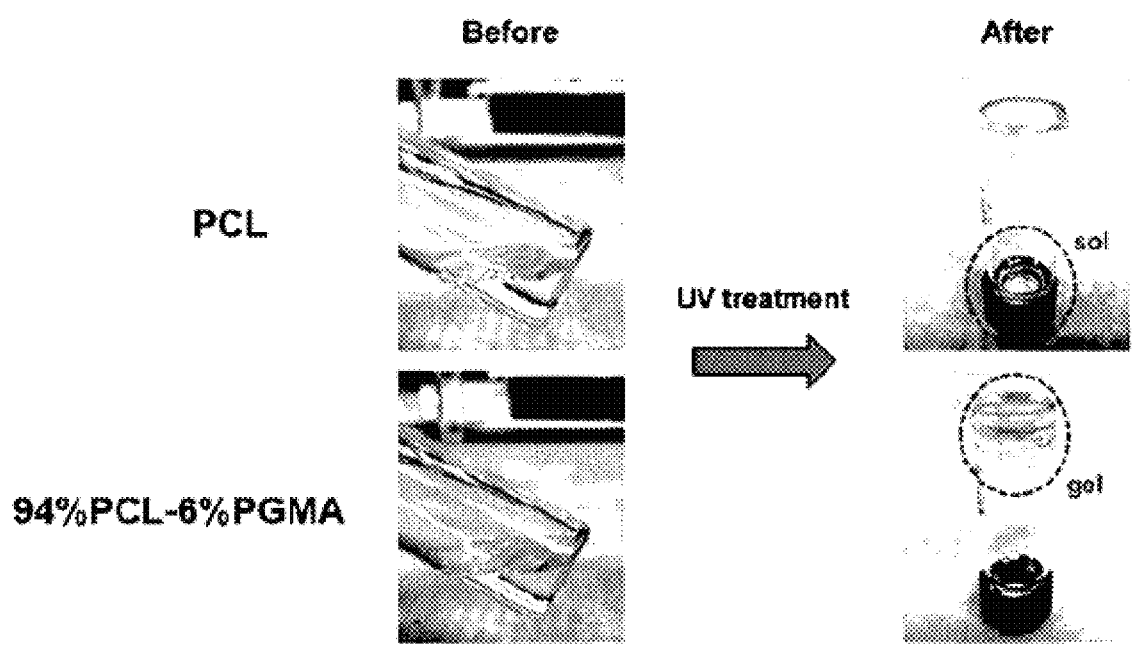
FIG. 13 shows the comparison of phenomena shown after UV treatment of the polymers of Example 1-2 and Comparative Example 1 prepared by the present invention.

FIG. 13 shows the comparison of phenomena shown after UV treatment of the polymers of Example 1-2 and Comparative Example 1.

Referring to FIG. 13, each of the polymer synthesized in Example 1-2 and the polymer synthesized in Comparative Example 1 was mixed with a photo-initiator at a volume ratio of 10:1, and then approximately 400 μL of each was put in a transparent glass container.

More specifically, each of the polymer synthesized in Example 1-2 and the polymer synthesized in Comparative Example 1 was dispersed at 50 wt % in dichloromethane, the photo-initiator was dispersed at 10 wt % in dichloromethane, and then the resulting dispersions were mixed in a volume ratio of 10:1.

In addition, UV light (320-500 nm) at an intensity of 14 W/cm$^2$ was applied to the glass container for 10 minutes.

In addition, the UV-treated container was turned over.

As a result, it can be confirmed that the polymer prepared in Example 1-2 was not detached from the bottom, and the polymer was crosslinked into a gel through crosslinking between acryl groups modified by UV treatment, but Comparative Example 1 was not phase-changed into a liquid state.

That is, it was confirmed that the polymer synthesized in Example 1-2 can be crosslinked by UV.

1-2. DSC Analysis-1

Figure 14:
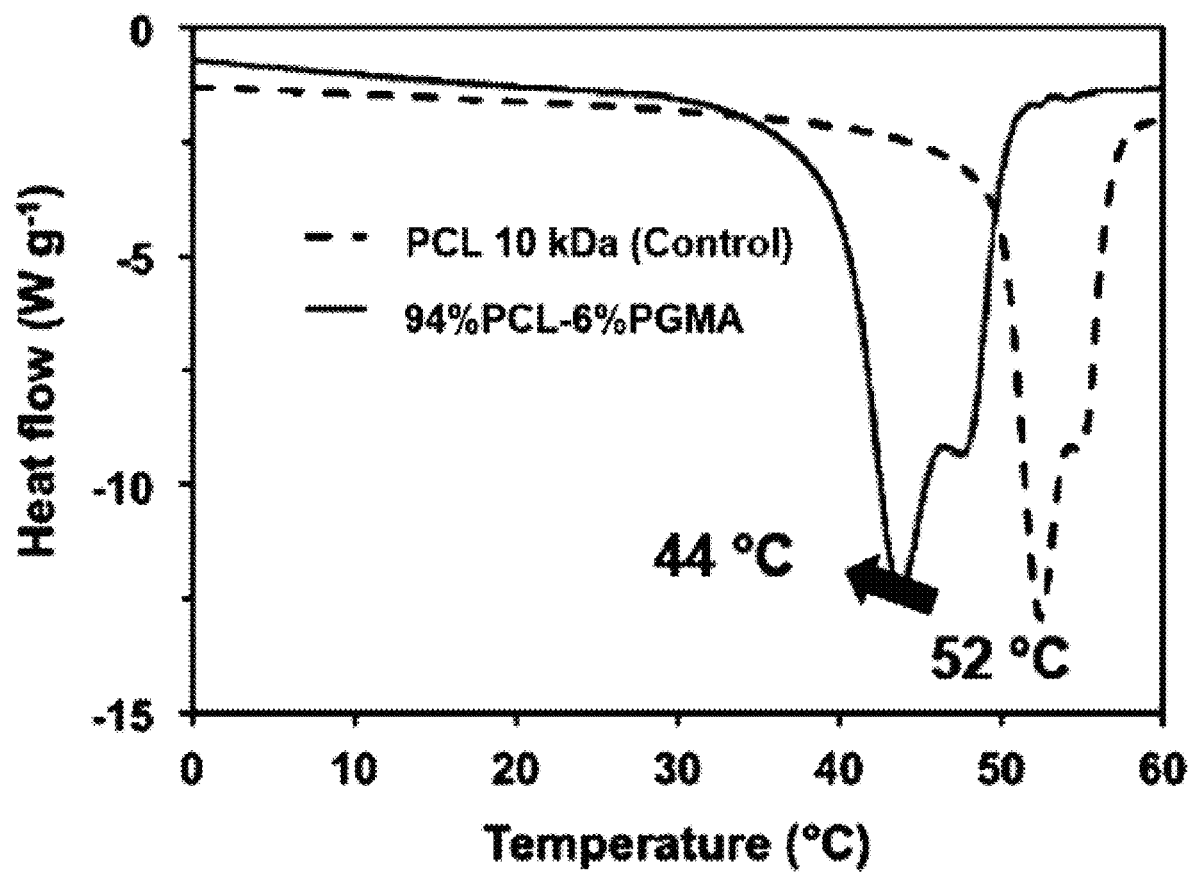
FIG. 14 is a graph of the differential scanning calorimetry (DSC) analysis for Example 1-2 and Comparative Example 1 prepared by the present invention.

FIG. 14 and Table 9 are a graph and a table representing DSC analysis for the polymers of Example 1-2 and Comparative Example 1.

More specifically, to analyze properties affected by the composition and design variables of a polymer, differential scanning calorimetry (DSC) was used ($T_m$; melting temperature, $\Delta H_m$; melting enthalpy, $T_c$; crystallization temperature, $\Delta H_c$; crystallization enthalpy).

TABLE 9

| Polymer | $T_m$(° C.) | $\Delta H_m$(J/g) | $T_c$(° C.) | $\Delta H_c$(J/g) |
|---|---|---|---|---|
| Comparative Example 1 | 52.41 | 78.85 | 24.13 | 79.49 |
| Example 1-2 | 43.76 | 55.97 | 20.95 | 57.00 |

Referring to FIG. 14 and Table 9, it was confirmed that the melting temperature of the PCL-co-PGMA synthesized in Example 1-2 can be lower than that of the PCL of Comparative Example 1 which was synthesized alone.

1-3. DSC Analysis-2

Figure 15:
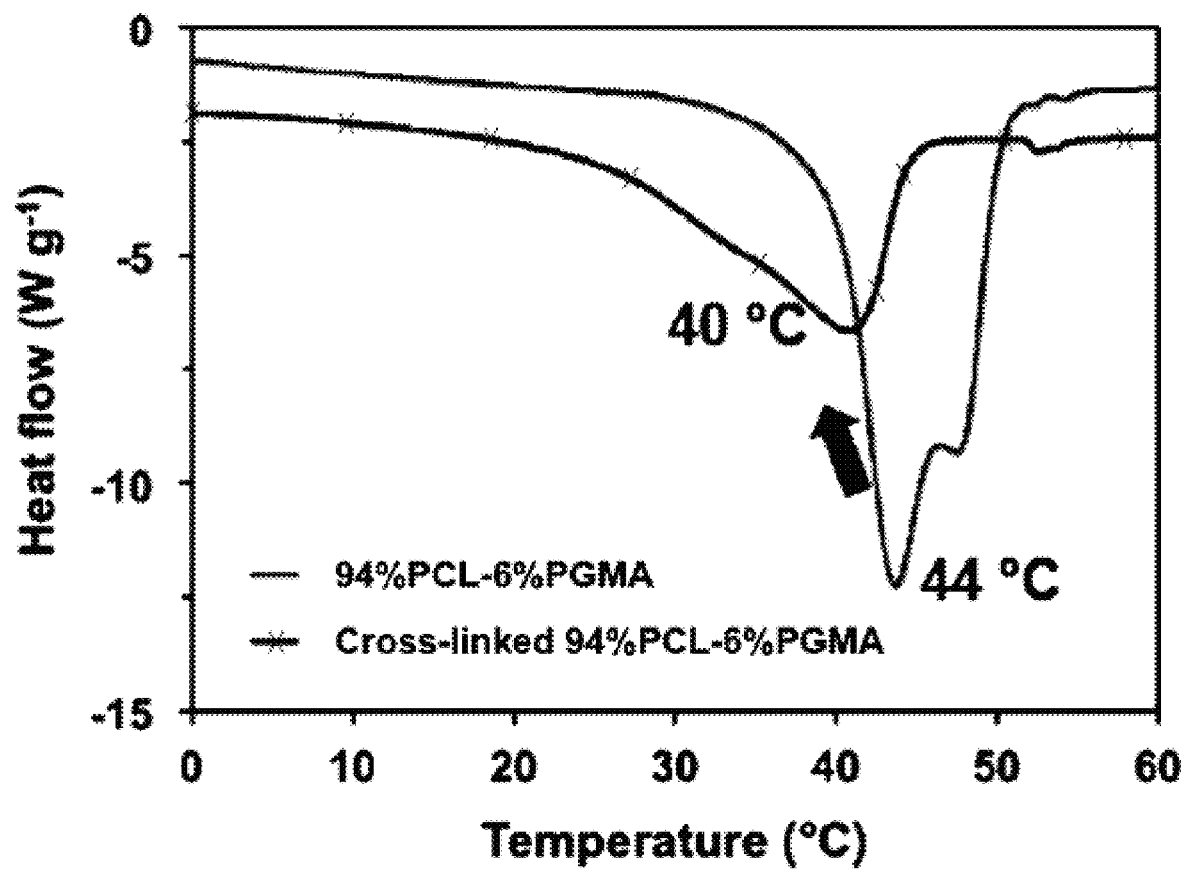
FIG. 15 is a graph of the DSC analysis for Example 1-2 and Comparative Example 1 prepared by the present invention after UV treatment.

FIG. 15 and Table 10 are a graph and a table representing DSC analysis after UV treatment of the polymers of Example 1-2 and Comparative Example 1.

TABLE 10

| Polymer | $XT_m$(° C.) | $\Delta H_m$(J/g) | $XT_c$(° C.) | $\Delta H_c$(J/g) |
|---|---|---|---|---|
| Comparative Example 1 | 52.05 | 67.17 | 23.17 | 65.17 |
| Example 1-2 | 40.44 | 43.01 | −1.73 | 26.32 |

Referring to FIG. 15 and Table 10, it was confirmed that the melting temperature of the PCL-co-PGMA synthesized in Example 1-2 was lower than that of the PCL of Comparative Example 1 which was synthesized alone, and particularly, after the UV treatment of the polymer synthesized in Example 1-2, the melting temperature was lowered to 40.44° C. from when UV treatment was not performed.

Experimental Example 2. Analysis of Characteristics Before and After UV Crosslinking of SMPs Prepared in Examples 1-1 to 1-3

In Experimental Example 2, mechanical and thermal characteristics of the polymers synthesized in Examples 1-1 to 1-3 before and after UV crosslinking were analyzed.

Figure 16:
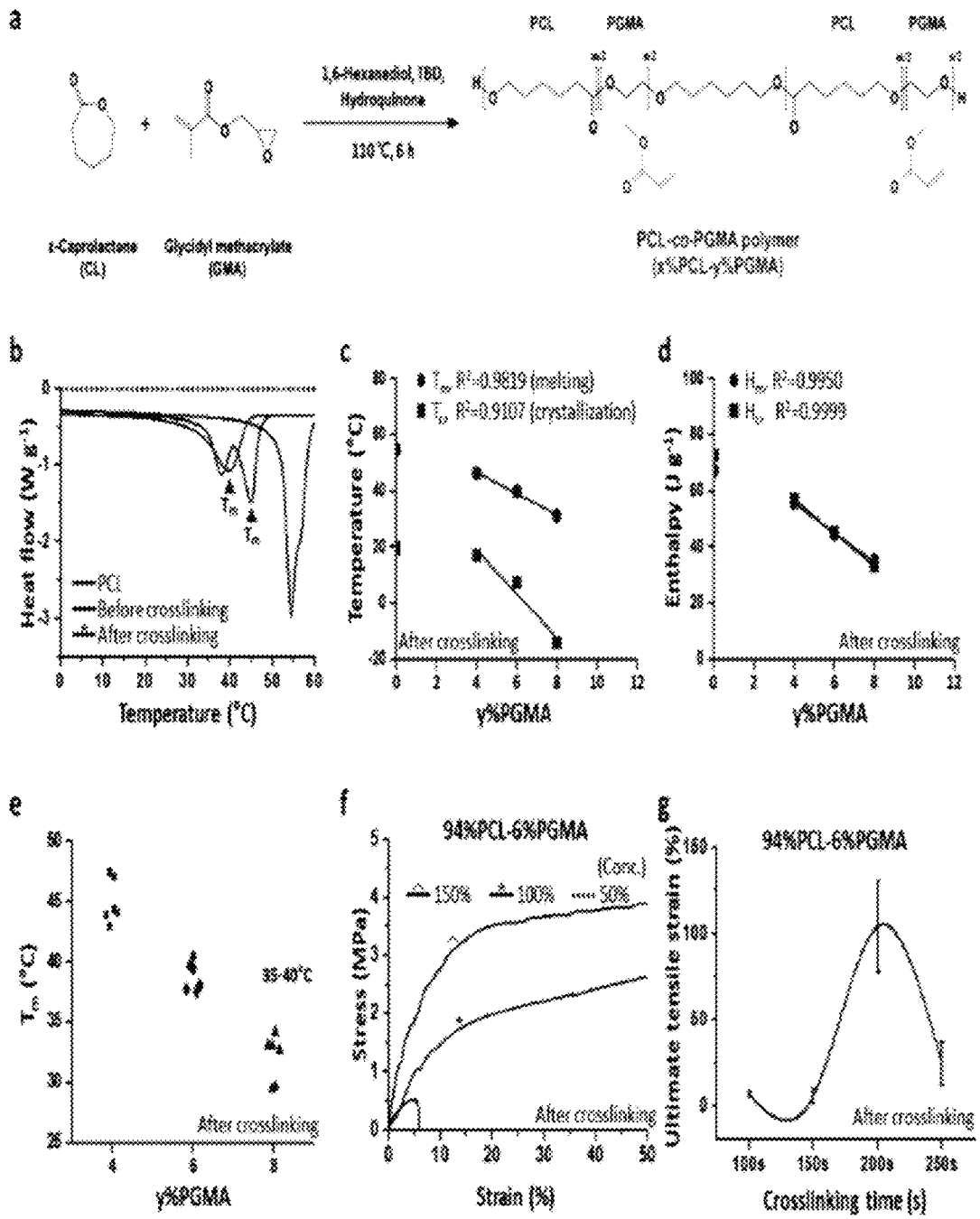
FIG. 16 shows the synthesis scheme of a shape-memory polymer of the present invention and the result of evaluating the mechanical and thermal characteristics of shape-memory polymers prepared in Examples 1 and 2 ((a) the synthesis scheme and structure of a shape-memory polymer, (b) the result of analyzing melting temperatures for a shape-memory polymer before and after UV crosslinking (DSC), (c) to (e) changes in thermal characteristics ($T_m$, $T_c$, $H_m$ and $H_c$) according to the change in PGMA content, (f) determination of shape-memory polymer concentration after crosslinking through analysis of stress-strain curves, (g) determination of optimal crosslinking time of 94% PCL-co-6% PGMA).

The results are shown in FIG. 16 and Table 11.

TABLE 11

| | | Characterizations | | | | |
|---|---|---|---|---|---|---|
| | Polymer | Theoretical x (%) | Actual x (%) | $M_n$ (Da) | $M_w$ (Da) | PDI |
| Before Crosslinking | 100% PCL | 100 | 100.00 | 18.104 | 27.418 | 1.51 |
| | 96% PCL-4% PGMA | 96 | 96.50 | 10.184 | 16.198 | 1.59 |
| | 94% PCL-6% PGMA | 94 | 94.38 | 9.828 | 14.286 | 1.45 |
| | 92% PCL-8% PGMA | 92 | 93.60 | 7.967 | 10.458 | 1.31 |

| | | Mechanical properties | | |
|---|---|---|---|---|
| | Polymer | E (37° C.) (MPa) | $\varepsilon_{max}$ (%) | $\sigma_{max}$ (MPa) |
| After Crosslinking | 96% PCL-4% PGMA | 111 ± 5.0 | 23.2 ± 6.7 | 6.16 ± 0.35 |
| | 94% PCL-6% PGMA | 24.7 ± 11 | 104 ± 26 | 3.65 ± 0.60 |
| | 92% PCL-8% PGMA | 3.82 ± 0.92 | 31.7 ± 21 | 0.649 ± 0.27 |

TABLE 11-continued

| | | Characterizations | | | | | |
|---|---|---|---|---|---|---|---|
| | | Thermal properties | | | | | |
| | Polymer | $T_m$ (° C.) | $\Delta H_m$ (J g$^{-1}$) | $X_c$ (%) | $T_c$ (° C.) | $\Delta H_c$ (J g$^{-1}$) | $T_g$ (° C.) |
| Before Crosslinking | 96% PCL-4% PGMA | 47.6 ± 2.7 | 62.2 ± 1.9 | 44.6 ± 2.2 | 17.3 ± 1.2 | 62.2 ± 3.1 | −57.8 ± 0.6 |
| | 94% PCL-6% PGMA | 43.9 ± 0.80 | 61.3 ± 4.4 | 44.0 ± 4.4 | 16.7 ± 3.1 | 61.6 ± 2.8 | −57.5 ± 1.3 |
| | 92% PCL-8% PGMA | 41.1 ± 0.63 | 59.9 ± 0.13 | 42.9 ± 4.6 | 15.2 ± 5.2 | 57.9 ± 5.6 | −56.7 ± 1.1 |
| After Crosslinking | 96% PCL-4% PGMA | 46.2 ± 1.7 | 55.8 ± 3.4 | 40.8 ± 2.7 | 17.0 ± 2.1 | 57.0 ± 3.8 | −53.0 ± 1.0 |
| | 94% PCL-6% PGMA | 39.9 ± 0.53 | 44.5 ± 3.5 | 32.4 ± 3.2 | 7.21 ± 0.78 | 45.1 ± 4.5 | −52.0 ± 0.59 |
| | 92% PCL-8% PGMA | 31.1 ± 2.7 | 35.0 ± 3.6 | 23.7 ± 2.8 | −14.3 ± 9.4 | 33.1 ± 3.9 | −57.6 ± 1.9 |

Referring to FIG. 16 and Table 11, it was confirmed that, when comparing the characteristics of Examples 1-1 to 1-3, it was confirmed that the melting temperature of the PCL-co-PGMA synthesized in Examples 1-1 to 1-3 was lower than that of the PCL synthesized alone like Comparative Example 2 (FIG. 16B).

In addition, referring to FIG. 16, as a result of confirming a molecular weight through GPC analysis, it was confirmed that a target level is Mw 10 kDa or less. Particularly, it was confirmed that, as a GMA content increases, a molecular weight was decreased. In addition, it can be seen that $T_m$ and % crystallinity are lowered due to amorphous PGMA disrupting PCL crystallinity (Table 11).

Particularly, it was confirmed that, as the GMA content increases, the melting temperature and the enthalpy values are lowered, and the melting temperature ($T_m$) of the polymer after UV treatment is lower than that when UV treatment was not performed (FIGS. 16B to 16D). Particularly, it can be confirmed that a melting temperature range of the UV-crosslinked 94% PCL-6% PGMA is in the body temperature range (FIG. 16E), and therefore it is expected that the SMP has high applicability as a vascular anastomotic member.

Since the maximum tensile strain had reached the maximum value (~100%) when the 94% PCL-6% PGMA SMP reached a time point of 200 seconds after UV crosslinking, the crosslinking time was determined to be 200 seconds (FIG. 16G).

Experimental Example 3. Confirmation of Recovery Ability of SMP

Figure 17:
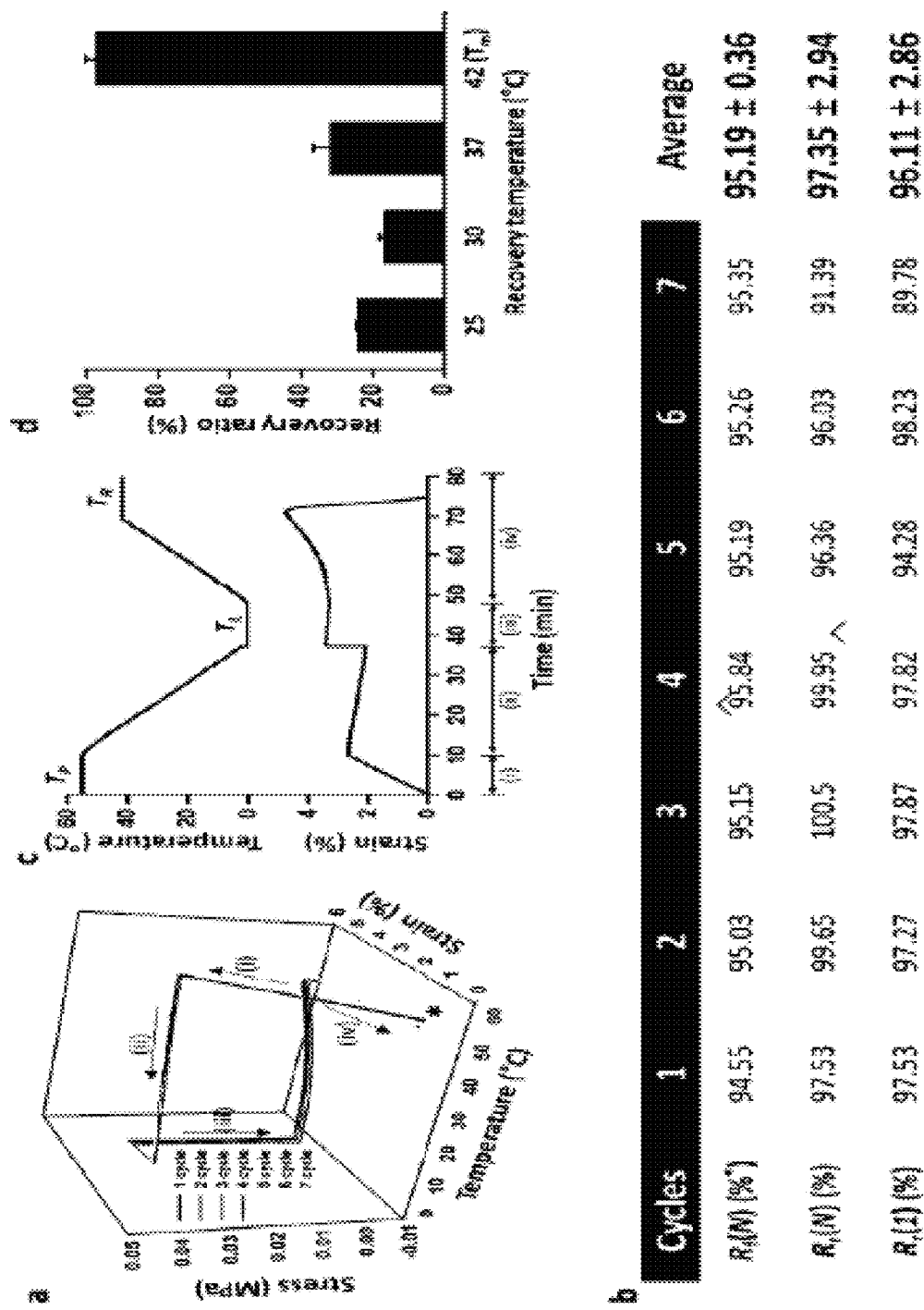
FIG. 17 shows the result of evaluating the shape memory property of UV crosslinked 94% PCL-co-6% PGMA ((a) the result of 7 cycles (N) or more of stress-controlled cyclic thermomechanical tensile tests, (b) the result of measuring an average shape recovery ratio [Rr(N) %] and a shape fixation ratio [Rf(N) %], (c) programmed time setting in (a) process, (d) shape recovery ratio according to temperature of 94% PCL-co-6% PGMA).

A shape memory property was investigated in 7 cycles (N) or more of stress-controlled cyclic thermomechanical tensile tests performed on DMA (FIG. 17A). (i) A 94% PCL-6% PGMA film was heated to 55° C., and maintained equilibrium for 10 minutes [εp(0), initial permanent shape], and the film was elongated by applying tensile stress at 4 kPa·min$^{-1}$ until reaching 39 kPa. (ii) After the film was cooled to 0° C. at a rate of 2° C.·min$^{-1}$ and equilibrated for 10 minutes [ε1(N), maximum strain], (iii) the applied tensile stress was removed (4 kPa·min$^{-1}$) [cu (N), temporary shape]. (iv) Subsequently, the temperature was increased to 42° C. at a rate of 2° C.·min$^{-1}$ for recovery of a permanent shape [εp(N)]. For each cycle (N), the strain recovery rate [Rr(N) %] refers to the ability of the SMP to recover its original permanent shape [εp(N)] after deformation, and the strain precision [Rf(N) %] refers to an ability of maintaining a temporary shape after removal of tensile stress, and calculated by the following equation.

$$R_r(N) = \frac{\varepsilon_1(N) - \varepsilon_p(N)}{\varepsilon_1(N) - \varepsilon_p(N-1)} \times 100\%; R_f(N) = \frac{\varepsilon_u(N)}{\varepsilon_1(N)} \times 100\%$$

As a result, as the shape recovery rate of the UV-treated 94% PCL-co-6% PGMA SMP material is 96% or more, the shape precision is 95% or more, it was confirmed that it has excellent recovery (FIG. 17B). In addition, the temperature-dependent change of strain (%) made it possible for shape memory ability to be programmed according to a specific time frame (FIG. 17C).

As a result of investigating the temperature-dependent shape recovery rate, it was confirmed that, when the temperature was less than the melting temperature (Tm), the shape recovery was less than 30%, but at the corresponding melting temperature, almost 100% recovery was shown (FIG. 17D).

Experimental Example 4. Characteristic of Vascular Anastomotic Member 4-1. Characteristics of Vascular Anastomotic Member The vascular anastomotic member prepared in Example 3 was separated from a mold.

Considering the melting temperature of the vascular anastomotic member, the inner diameter of the vascular anastomotic member changed by precipitation in 35 to 40° C. water was measured.

As a result, the inner diameter was 4 mm at 35 to 40° C., and the vascular thickness was 100 μm. It was determined that the vascular anastomotic member with an inner diameter of 4 mm can be applied to a blood vessel.

4-2. Measurement of Tensile Strength of Vascular Anastomotic Member

The tensile strength of the vascular anastomotic member of Experimental Example 4-1 was measured using a universal testing machine (3366, Instron). Specifically, after the cross-sectional area of the vascular anastomotic member was measured, it was mounted on a jig connected to a load cell and pulled it at 20 mm/min to measure the maximum tensile strength and strain at the point of failure of the vascular anastomotic member. The measured maximum tensile strength was compared with the maximum tensile stress calculated as a strength per unit area. As a result, the tensile strength of the vascular anastomotic member was 0.03 to 150 N/mm$^2$, and the strain was changed from 2 to 350%.

4-3. Measurement of Fluid Flow According to Thickness of Vascular Anastomotic Member A vascular anastomotic member was manufactured by the same method as described in Example 3, and when applied to a blood vessel, the blood vessel was modeled to measure whether a fluid vortex may occur, and the fluid flow in the blood vessel was simulated.

A device for simulating a fluid flow used an ANSYS program, and a Fluent module in the program. In addition, the outer diameter of the applied blood vessel was set to be 2.0 mm, and the inner diameter thereof was set to be 1.8 mm. In addition, the vascular anastomotic member applied to the target blood vessel was set to have a length of 5 mm and an outer diameter of 1.8 mm. Meanwhile, the sectional thickness of the vascular anastomotic member was set to be 100, 200 or 300 μm.

Figure 18:
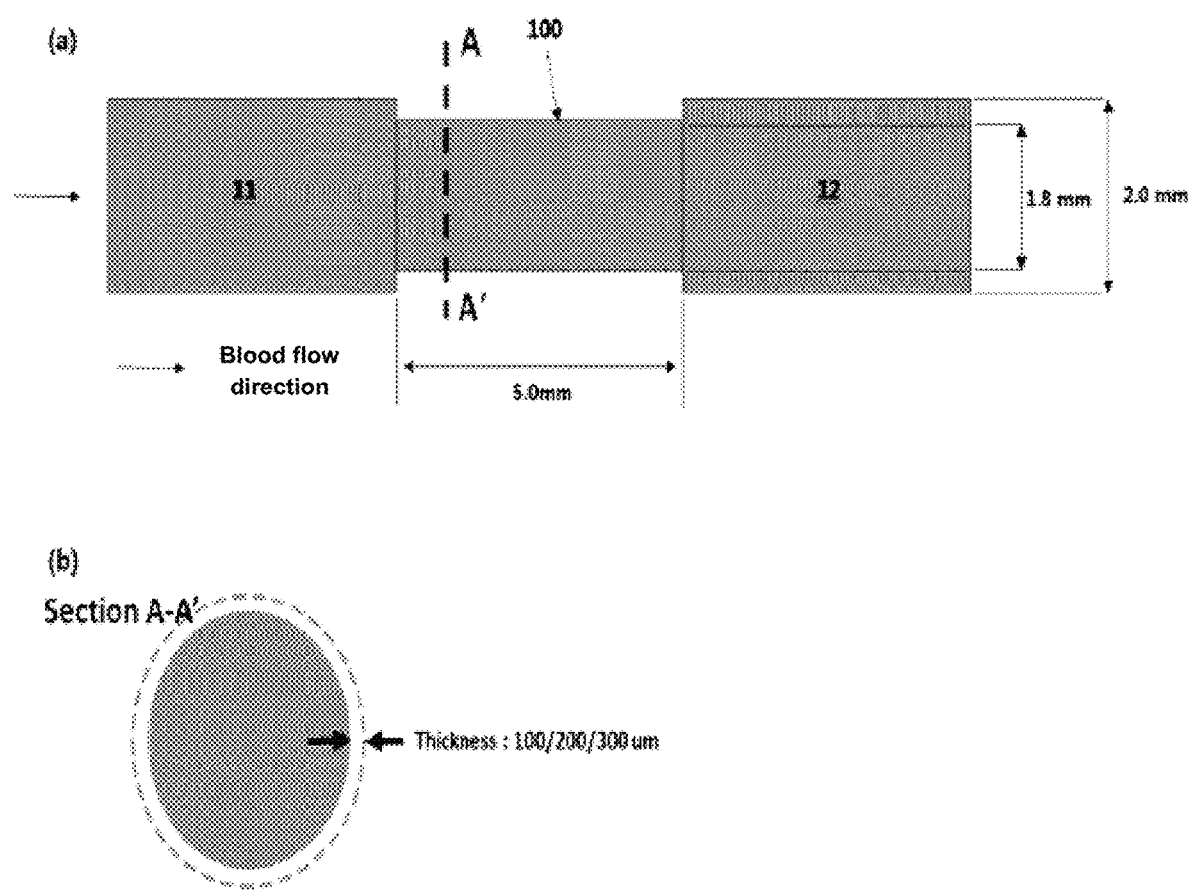
FIG. 18 shows a blood vessel for simulating a fluid flow (FIG. 18A: blood vessel to which a vascular anastomotic member is applied, FIG. 18B: cross-section view of vascular anastomotic member).

A blood vessel for simulating a fluid flow is shown in FIG. 18 (FIG. 18A: a blood vessel to which the vascular anastomotic member was applied, FIG. 18B: the cross-sectional view of the vascular anastomotic member).

Figure 19A:
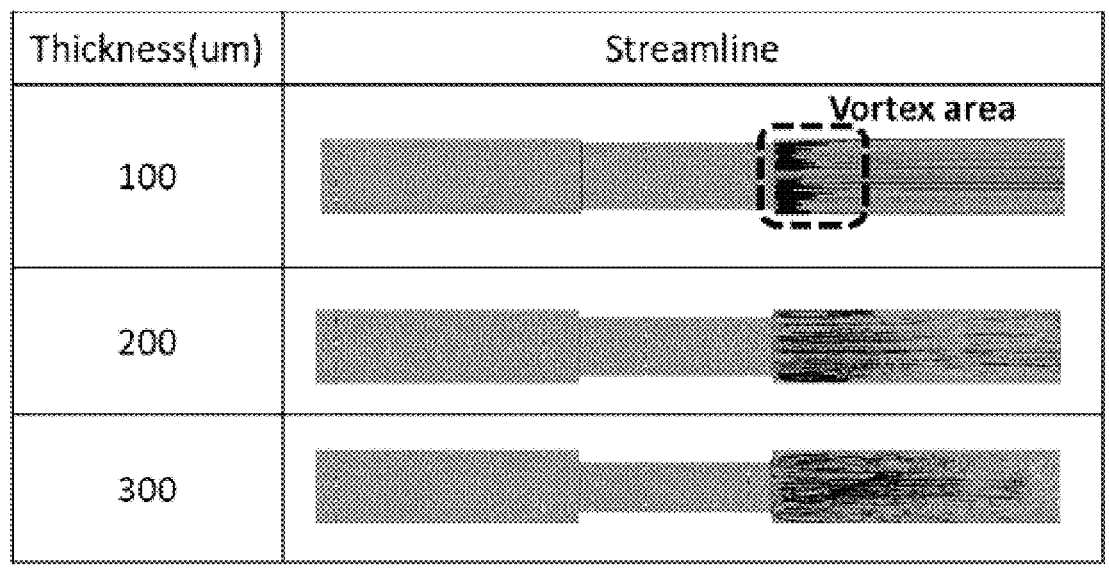
FIG. 19A shows a streamline according to the cross-sectional thickness of a vascular anastomotic member.
Figure 19B:
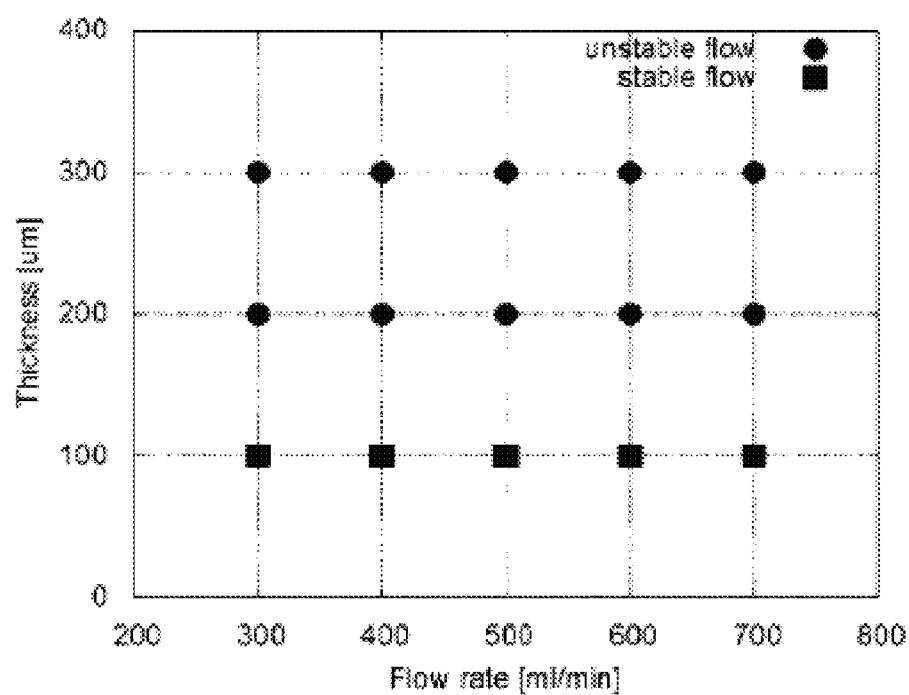
FIG. 19B shows the presence or absence of vortex formation in a graph of a flow rate and the sectional thickness of a vascular anastomotic member.
Figure 20:
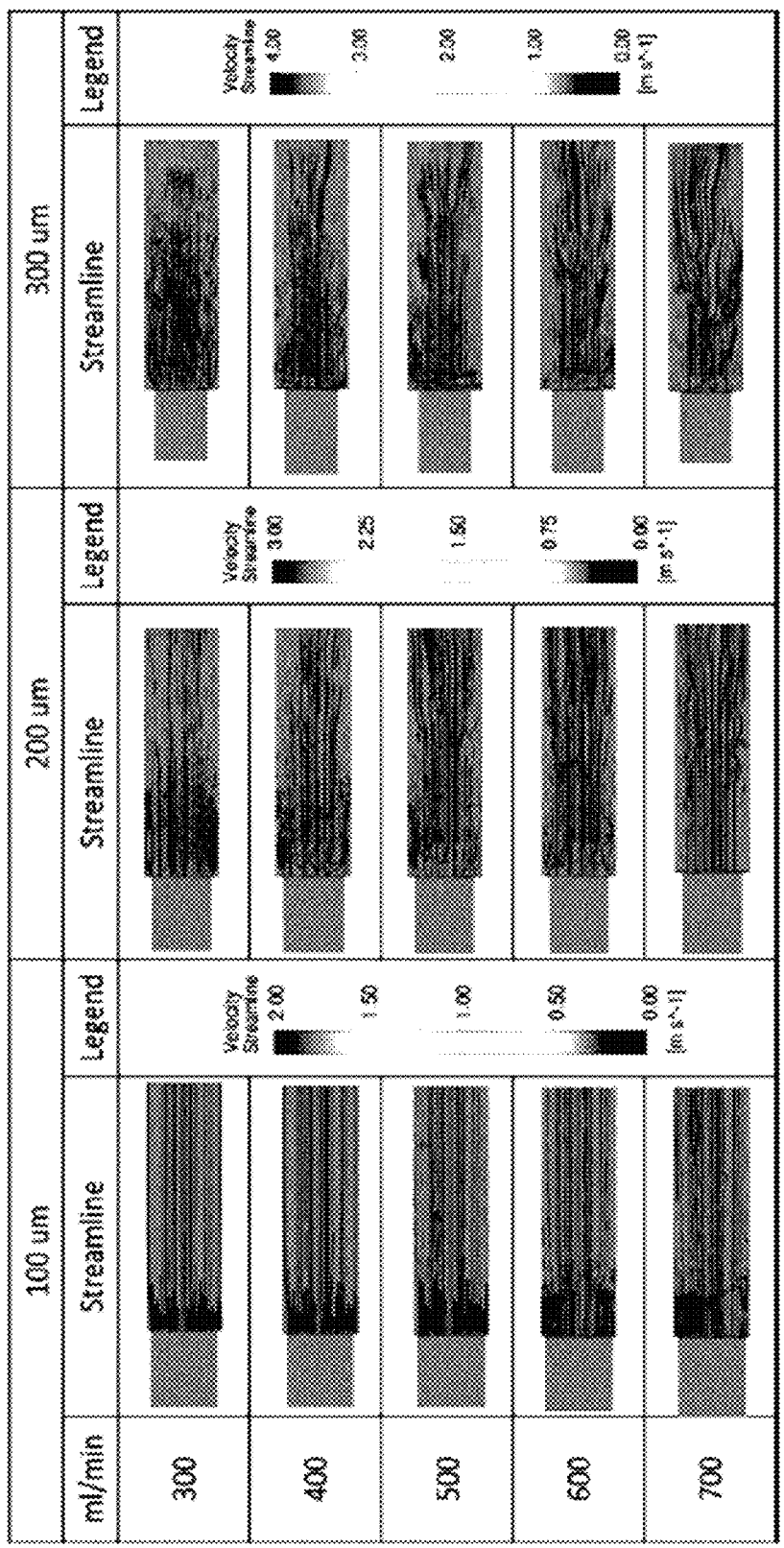
FIG. 20 shows a streamline according to the sectional thickness of a vascular anastomotic member.

In the simulation system, the flow rate was set to be 300 or 700 ml/min, and a streamline according to the sectional thickness of the vascular anastomotic member was measured and shown in FIGS. 19 and 20. FIG. 19A shows a streamline according to the sectional thickness of the vascular anastomotic member, and FIG. 19B shows a graph representing the presence or absence of vortex formation in the graph of a fluid rate and the sectional thickness of the vascular anastomotic member.

In addition, FIG. 20 shows a streamline according to the sectional thickness of the vascular anastomotic member.

Referring to FIGS. 19 and 20, due to the step difference between a blood vessel and the vascular anastomotic member, it was confirmed that a vortex was formed at a site where the blood vessel and the vascular anastomotic member are bound. Specifically, when vortexing was modeled at a thickness of 100, 200 or 300 μm, a vortex was strongly generated at 300 μm, and considerably reduced from 200 μm, and measured to be almost absent at 100 μm.

Particularly, even when the sectional thickness of the vascular anastomotic member was 100 μm, a vortex was generated, but it does not affect the flow of a fluid. That is, when the step difference between the inner diameter of the vascular anastomotic member and the inner diameter of a blood vessel is set to be less than 200 μm, it could be determined that the flow of the blood flow is smooth.

Experimental Example 5. Characteristics of SMP 5-1. Measurement of Characteristics Analysis According to SMP Concentration Changes in crosslinking degree and melting temperature were measured by changing a concentration of the 94% PCL-co-6% PGMA polymer synthesized in Example 1-2.

Specifically, the changes were measured by the following method.

Crosslinking Degree (%)

The composition of the synthesized polymer (the repeat unit ratio of PCL and PGMA according to the ratio of the number of hydrogen atoms of PCL and PGMA) were measured using $^1$H NMR (nuclear magnetic resonance).

Melting Temperature (° C.)

To analyze the melting temperature of the polymer, DSC was used.

TABLE 12

| | | Crosslinking degree (%) | Melting temperature (° C.) |
|---|---|---|---|
| Example 1-2-1 | 50 w/v % | 83.72 ± 1.71 | 37.56 |
| Example 1-2-2 | 75 w/v % | 83.34 ± 1.46 | 37.03 |
| Example 1-2-3 | 100 w/v % | 84.26 ± 1.41 | 37.77 |

As a result, as shown in Table 12, it can be confirmed that a crosslinking degree and a melting temperature are changed according to the concentration of the SMP dissolved based on a solvent. That is, it was confirmed that the crosslinking degree and melting temperature (shape recovery temperature) can be adjusted by adjusting the concentration % of the SMP dissolved in the solvent. In addition, as a result of testing the viscosity and shear viscosity according to a strain by varying the concentration of the 94% PCL-6% PGMA polymer, at the polymer concentration of 100% (w/v), when the strain of the test concentration was increased to 50%, it was confirmed that the stress was increased to approximately 2 MPa, which is consistent with the behavior of actual blood vessels. When the polymer concentration is 200% (w/v), it was confirmed that the stress increases up to 4 MPa, which can damage blood vessels. When the polymer concentration is 50% (w/v), the SMP was torn at 5% strain due to a decrease in crosslinking degree due to an insufficient concentration, and loose bonds between the polymers (FIG. 16F).

5-2. Measurement of Contact Angle of SMP

Figure 21:
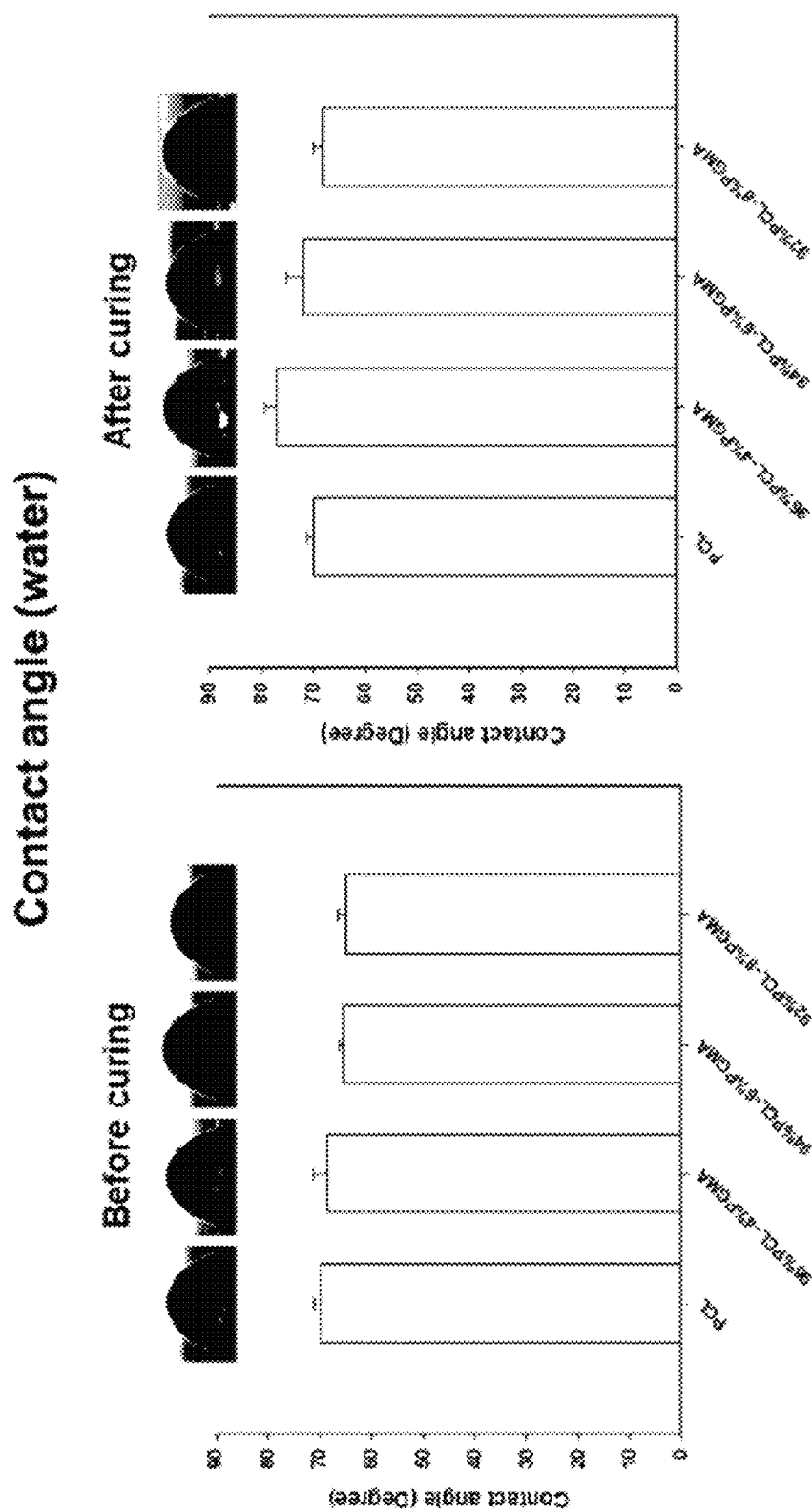
FIG. 21 shows the result of measuring a contact angle after a droplet (10 μg) of distilled water was dropped on the surface of a polymer of Comparative Example 1 (PCL) or a shape-memory polymer (96% PCL-co-4% PGMA polymer, 94% PCL-co-6% PGMA polymer, 92% PCL-co-8% PGMA polymer) before and after crosslinking.

A drop of distilled water (10 μg) was dropped on the surface of the polymer of Comparative Example 1 (PCL) or a SMP (the 96% PCL-co-4% PGMA polymer, the 94% PCL-co-6% PGMA polymer or the 92% PCL-co-8% PGMA polymer), the surface was photographed to analyze a contact angle, and then the result is shown in FIG. 21.

In addition, the SMPs of Comparative Example 1 were UV-crosslinked by the same method as described in Example 2, and a contact angle was analyzed by the same method as described above.

Referring to FIG. 21, before or after crosslinking, compared to PCL representing a polymer widely used as a biodegradable insert, it shows that there is no significant difference in hydrophobicity according to a composition.

Experimental Example 6. Evaluation of Suitability as Use for Vascular Anastomosis According to Shape of SMP Graft Material 6-1 Simulation of Selection of Shape of Vascular Anastomotic Member Consisting of SMP to Minimize Backflow and Disturbed Flow of Blood A flow field was designed for three graft member types (i.e., direct stepped, chamfer and diffuser) using CAD (SolidWorks Co.). The numerical simulation of each flow field was performed using Fluent (Ansys, Inc.) CFD solver. A non-linear Navier-Stokes equation controlling the conservation of mass and momentum within a fluid element was obtained. A Newtonian fluid was assumed to have blood properties at body temperature. The non-slip boundary condition was applied to all vessel walls. Mesh independence was verified by examining high-density meshes. The SIMPLE algorithm was implemented for pressure-velocity coupling, and entire space discretization was performed using a second order bottom-up approach. Density (1,060 kg·m$^{-3}$) and temperature (310K) were applied as the characteristics of a fluid in a tube-type graft material. The pulsating velocity profile in the aorta was considered under a flow input condition. This profile was reduced to mimic blood flow in the arteries, and the maximum velocity was set to be 45.0 cm·s$^{-1}$. The diameter of the graft material was 200 μm, and the Reynolds number based on the maximum velocity was 318, indicating a laminar regime. Accordingly, a Fluent lamina model was used for this simulation. For simulation analysis, systolic phase and diastolic phase peaks were generated using the Tecplot 360 (Tecplot, Inc.) post-processing program.

To verify the CFD simulation result, three different types (linear, direct stepped and diffuser) of microfluid devices were manufactured using a 3D printer. A microfluidic flow pattern was determined by perfusion of a red fluorescent sphere (diameter=4 μm, flow rate=10 ml·min$^{-1}$, Invitrogen). To evaluate cell sorting during flow, after fibronectin coating, human umbilical vein endothelial cells (HUVECs) were cultured for 24 hours in the device (1 μg·ml$^{-1}$). Subsequently, the culture medium was perfused at a flow rate of 10 ml·min$^{-1}$ for 48 hours. Subsequently, HUVECs were stained with TRITC-labeled phalloidin (Molecular Probes) to visualize a filamentous actin structure. The direction of microparticle flow and HUVEC alignment were analyzed through FFT analysis using the oval profile plugin (designed by William O'Connell) of ImageJ software (National Institutes of Health). All FFT results were normalized to compare data sets obtained from each microfluidic device using ORIGIN 8.0 software (OriginLab Corporation).

Figure 22A:
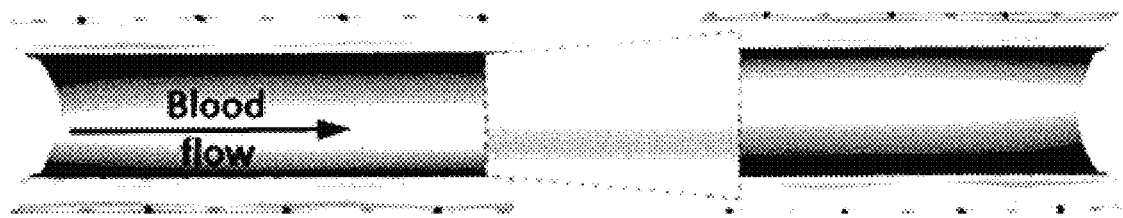
FIGS. 22A, 22B, 22C, 22D, 22E, 22F, 22G and 22H show the result of computer and microfluid simulation to determine the shape of a graft material including a shape-memory polymer suitable for vascular anastomosis: (a) the schematic diagram of intravascular transplantation of a diffuser-type model, (b) blood flow velocities in systolic and diastolic phases of the coronary artery, (c) and (e) the change in blood flow at the end of a transplanted blood vessel according to the shape of a graft material in a systolic phase, (d) and (e) the change in blood flow at the end of a transplanted blood vessel according to the shape of a graft material in a diastolic phase, and (f) to (h) microbeads in a microfluid device manufactured by reflecting a graft material shape and blood flow directions and flow simulation results predicted by HUVEC flow.
Figure 22B:
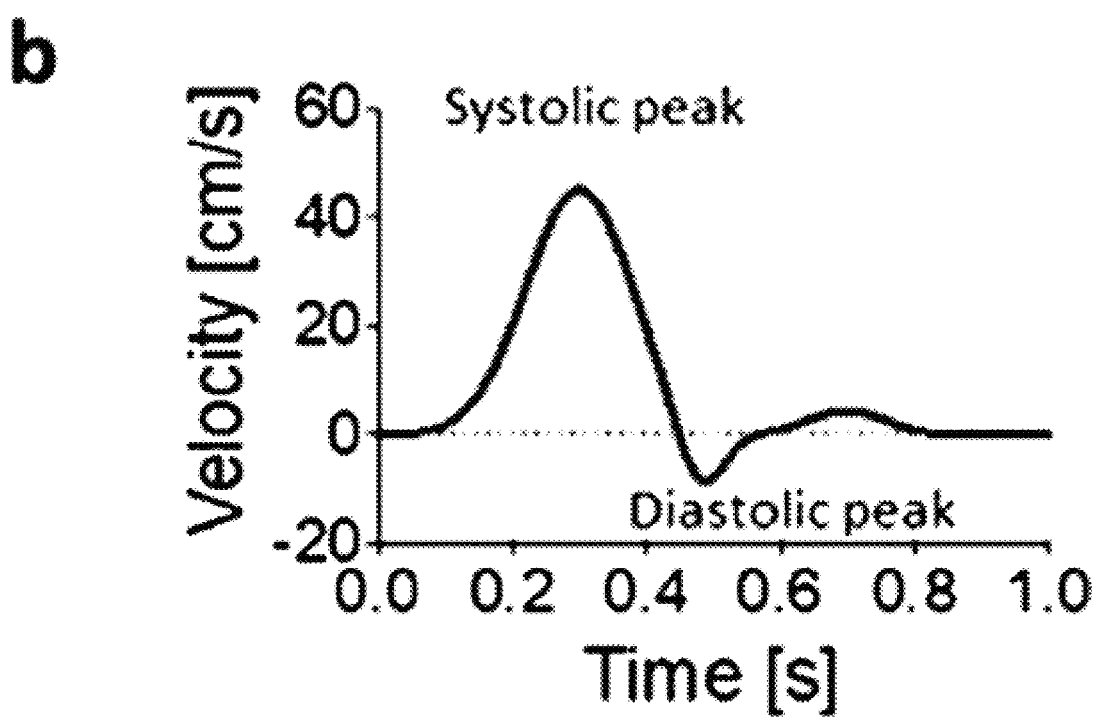
Figure 22C:
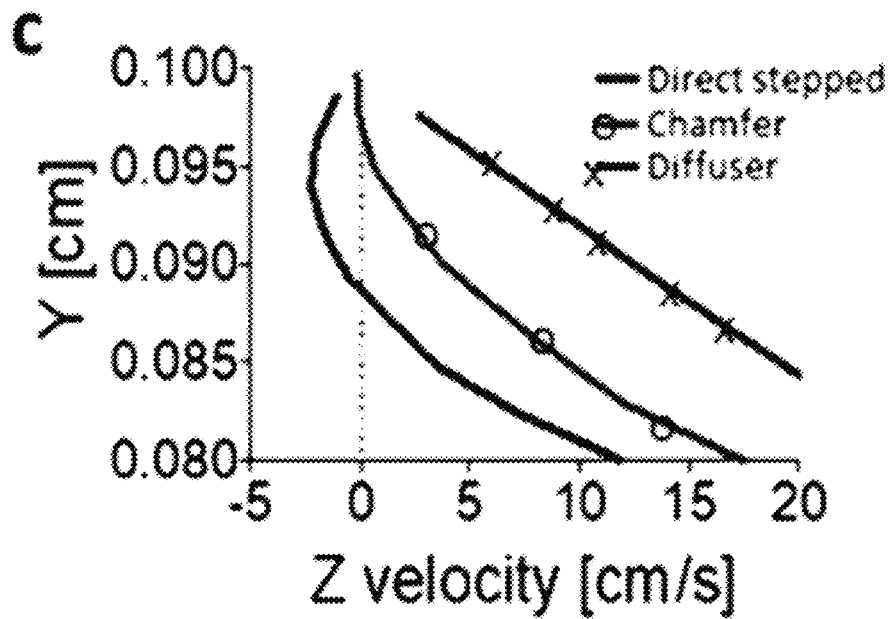
Figure 22D:
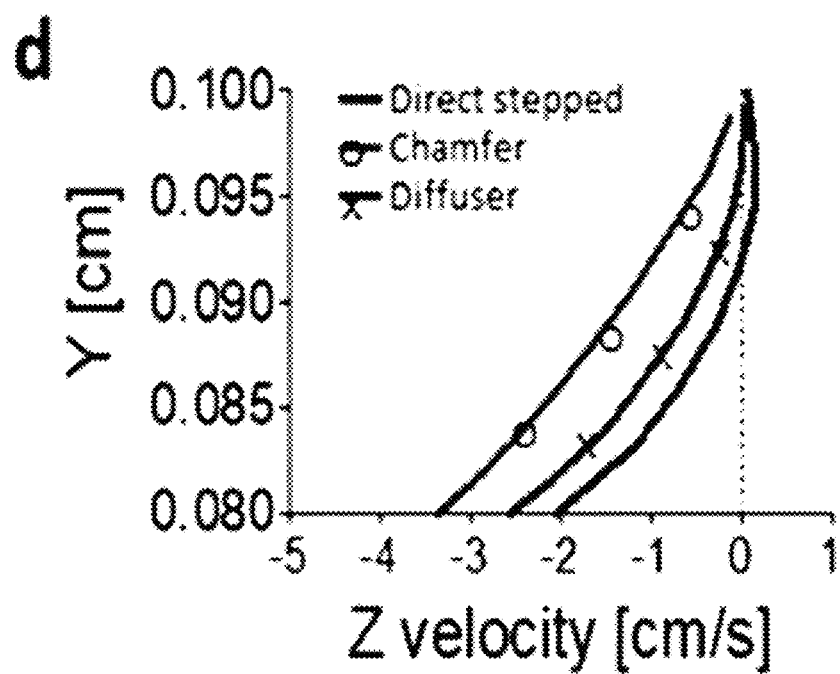
Figure 22E:
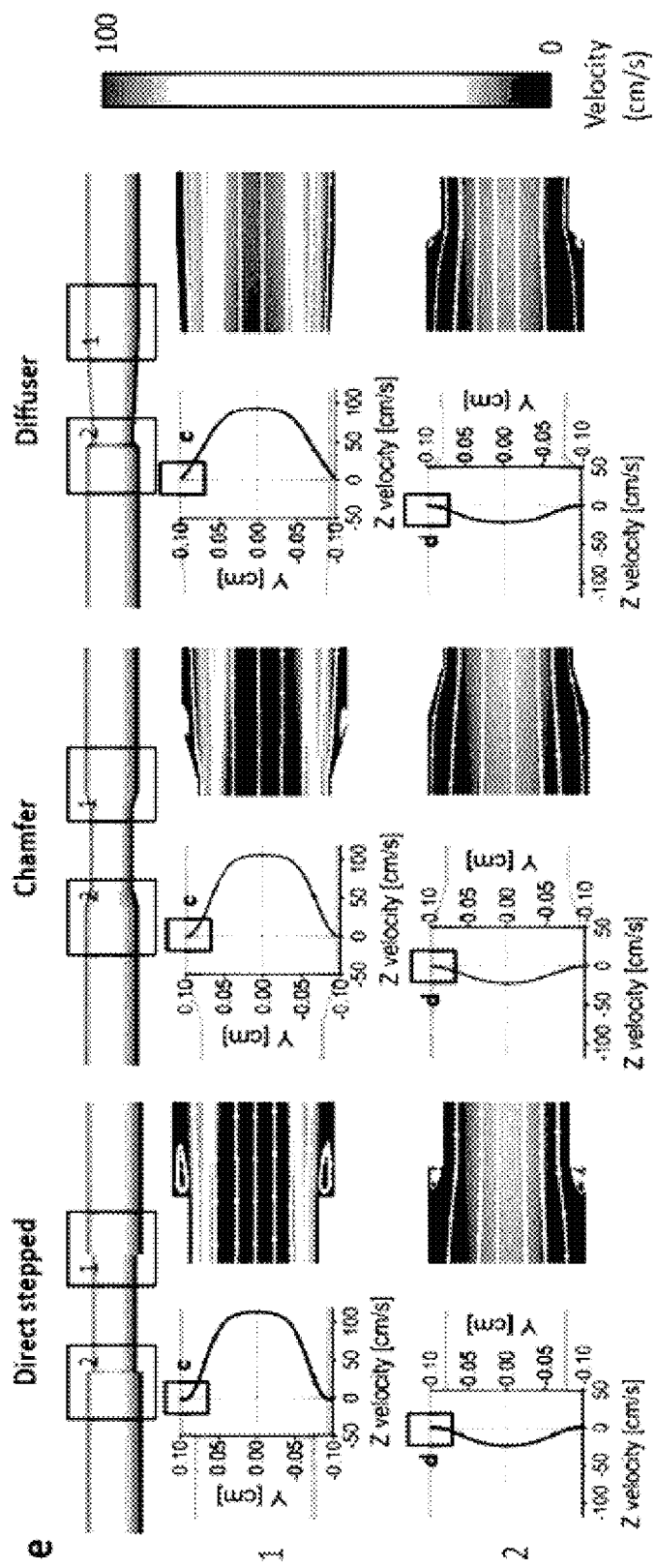

As a result, through the analysis of the Z velocity at a systolic phase peak, in a direct stepped model, it was confirmed that a disturbed flow was generated around an outlet site as well as a backflow. In a chamfer model, the disturbed flow was slightly reduced, but backflow stagnation was still observed around the outlet vessel wall. However, in a diffuser model, a disturbed flow was not observed (FIGS. 22C and 22E). On the contrary, as a result of the same velocity analysis at the diastolic phase peak, in the direct stepped model, a disturbed flow was generated on the inlet vessel wall. The disturbed flow was not observed in a chamfer-type model. Due to the backflow, a reduced disturbed flow was shown on the inlet vessel wall of the diffuser model (FIGS. 22D and 22E). However, the flow pattern appearing on the inlet vessel wall was not shown in the coronary artery in vivo. From the confirmed results, it was confirmed that a disturbed flow can be minimized when a diffuser model is selected as a structure of the blood vessel graft material.

Figure 22F:
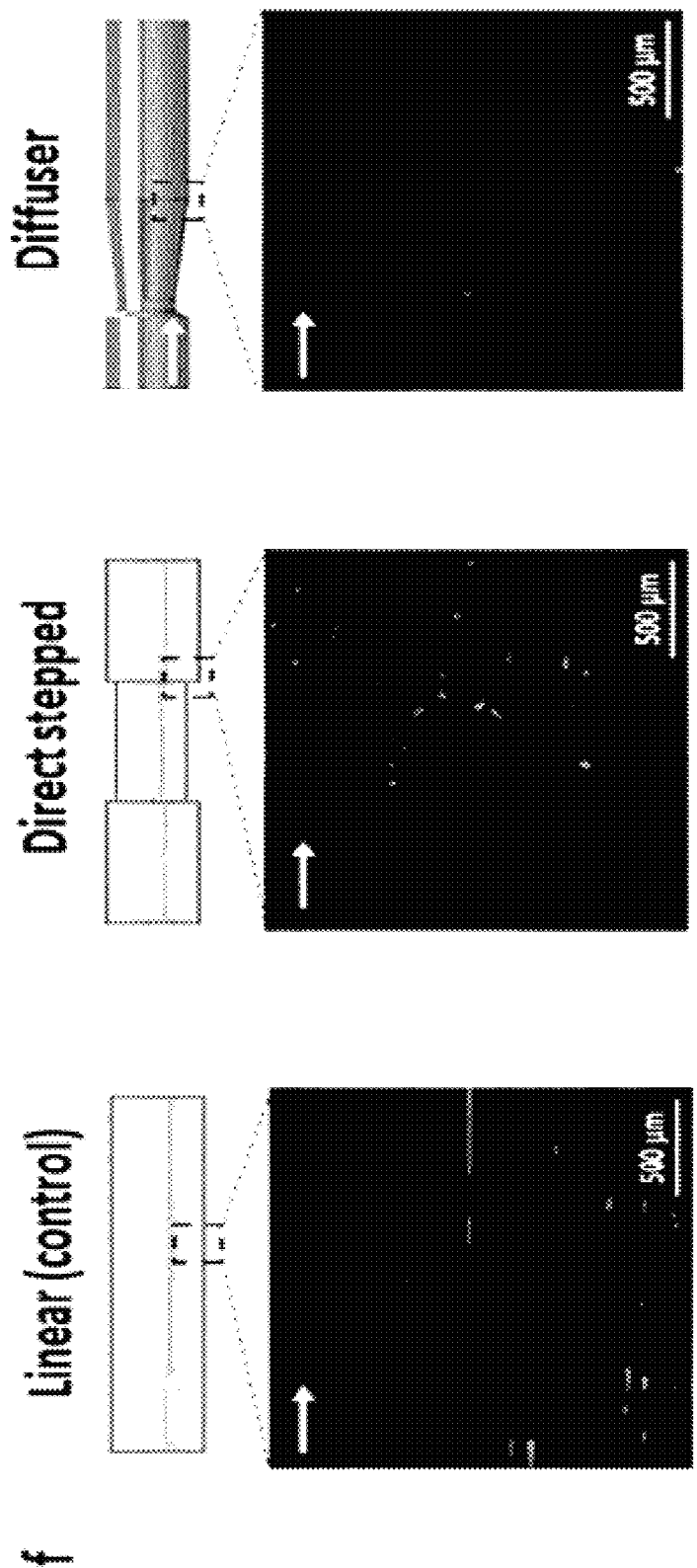
Figure 22G:
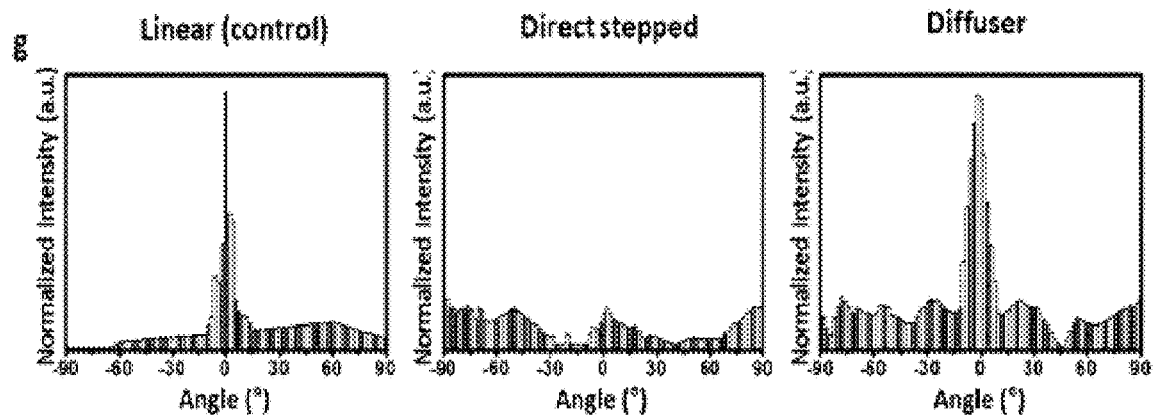
Figure 22H:
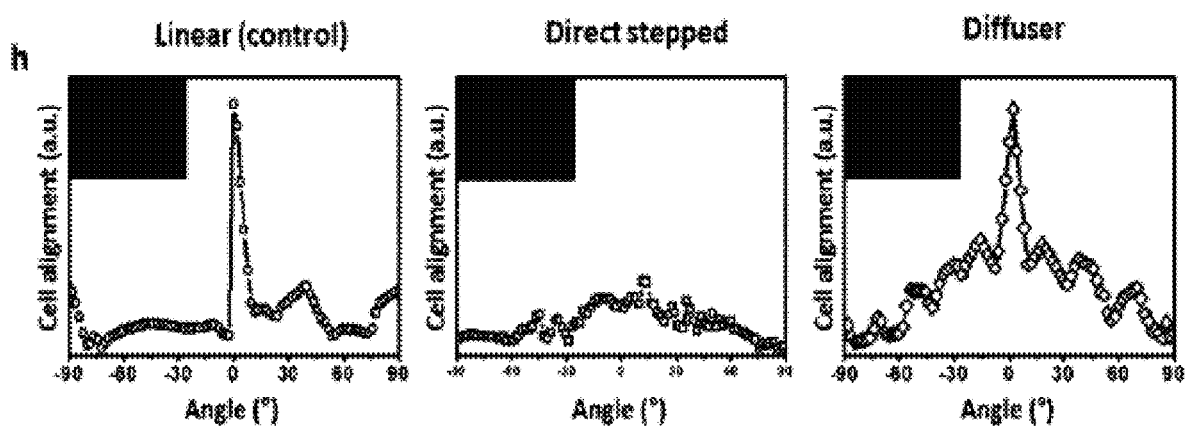
Figure 23:
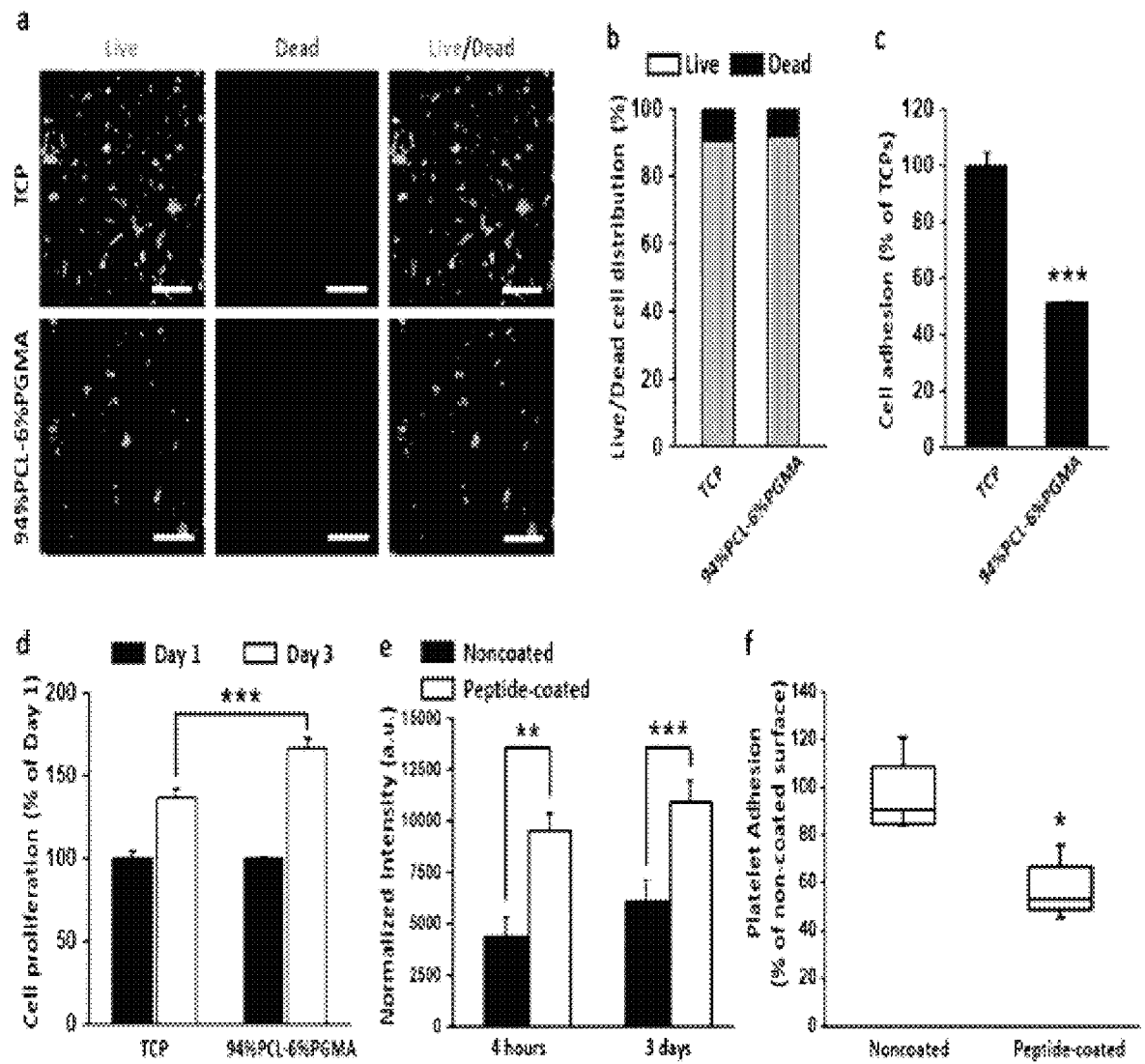
FIG. 23 shows the result of evaluating biocompatibility of a graft material for vascular anastomosis formed of a shape-memory polymer of the present invention.

In addition, as a result of analyzing a fluorescent particle flow and vascular endothelial cell (EC) alignment using three types (linear, direct stepped and diffuser) of microfluidic devices manufactured by 3D printing, it was confirmed that a disturbed flow was minimized in a diffuser model (FIG. 22F). This shows that the particle movement direction and the HUVEC alignment direction are most well matched with the flow direction of the diffuser model (angle=0°). This result was also supported by FFT analysis. Such a result indicates that the diffuser model is suitable for minimizing stenosis (FIGS. 22G and 22H).

Experimental Example 7. Evaluation of In Vivo Suitability of SMP Member for Vascular Anastomosis 7-1. Evaluation of In Vivo Suitability of SMP as Vascular Anastomotic Member HUVECs were cultured for 24 hours on a 94% PCL-6% PGMA film. Subsequently, cell viability was evaluated using live/dead staining (live cells: green; dead cells: red). The adhesion (6 hours) and proliferation rate (3 days) of HUVECs were determined using a cell counting kit-8. Relative cell proliferation at each time point was expressed by calculating cell viability (%) compared with a corresponding first day value.

Specifically, HUVEC adhesion evaluation was performed according to the method described in Kwon, H. J. et al. Acta Biomater. 61, 169-179 (2017).

To prevent coagulation of blood on the graft member, the 94% PCL-6% PGMA film was coated with a NO-releasing peptide amphiphilic substance (PA). The NO-releasing PA was synthesized according to Alexander, G. C. et al. ACS Biomater. Sci. Eng. 4, 107-115 (2017).

Figure 24:
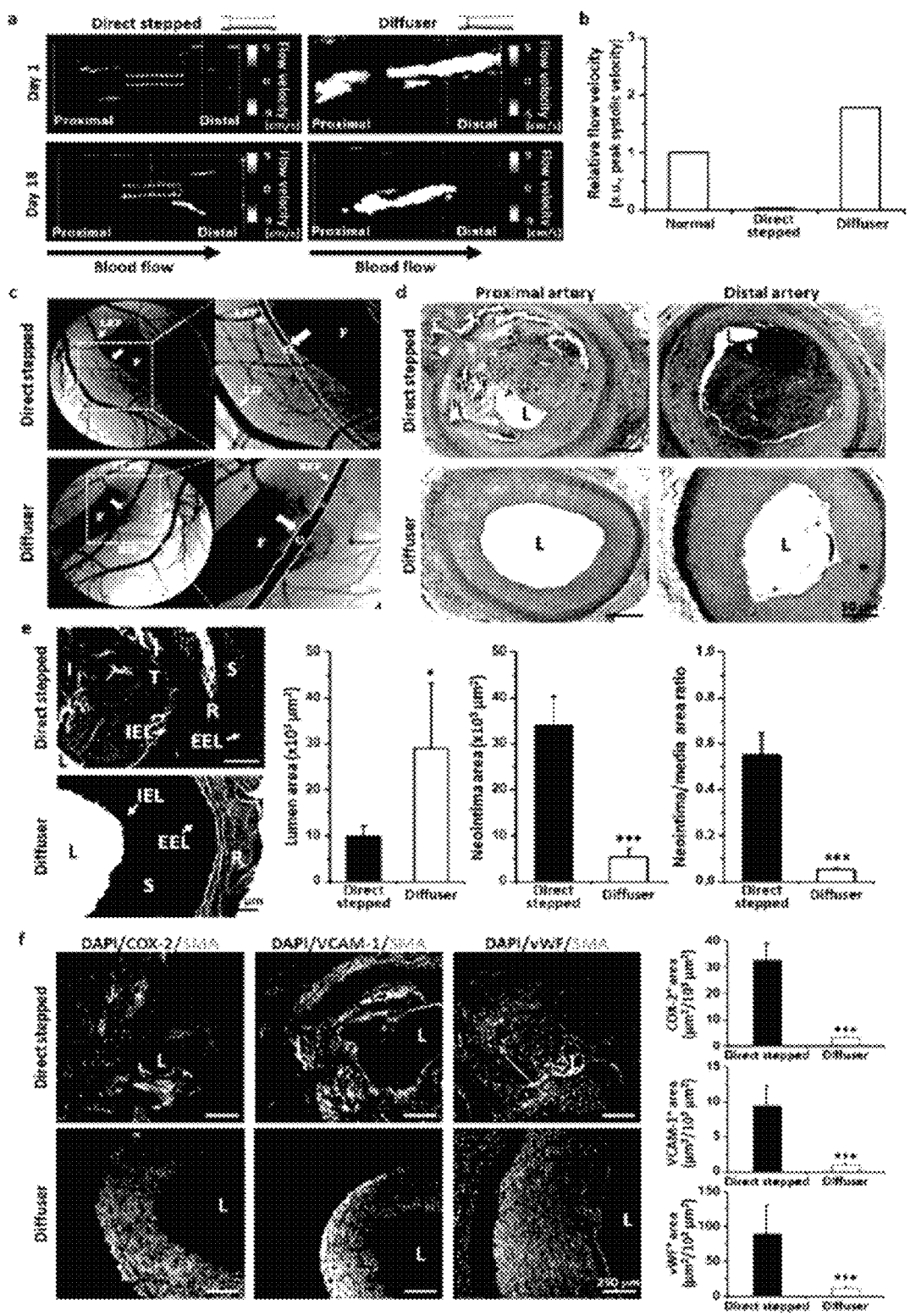
FIG. 24 shows the result of confirming vascular patency after a graft for shape-memory polymer vascular anastomosis of the present invention is transplanted into the femoral artery of a pig.

As a result, as shown in FIGS. 24A and 24B, it was confirmed that the HUVEC viability on the 94% PCL-6% PGMA film was similar to that of tissue culture plastic (TCP). In addition, the cell adhesion was shown to be approximately half of the adhesion of TCP (FIG. 24C). In addition, it was confirmed that the HUVEC cell proliferation rate on the 94% PCL-6% PGMA film was superior to that of TCP (FIG. 24D). As a result of comparing the cell proliferation rate and cell adhesion between the NO-releasing PA-coated 94% PCL-6% PGMA and non-coated 94% PCL-6% PGMA (FIG. 24D), it was confirmed that the cell proliferation rate of the NO-releasing PA-coated 94% PCL-6% PGMA was excellent, and the cell adhesion thereof was relatively low (FIGS. 24E and 24F). Taken together, the above results confirm that the NO-releasing PA-coated 94% PCL-6% PGMA is a material suitable for application to the living body.

7-2. Evaluation of Animal Transplantation of Vascular Anastomotic Member Consisting of SMP Diffuser and direct stepped graft materials were prepared by UV curing in a customized glass mold by the method of Example 3. According to the approved IACUC (No. 2017-0058) of Yonsei University Medical School, female Yorkshire pigs weighing 30 to 40 kg were used for a surgical procedure. Each pig was injected intramuscularly with atropine (0.04 mg·kg-1), xylazine (2 mg·kg$^{-1}$) and azaferon (2 mg·kg$^{-1}$). Subsequently, anesthesia was induced with Aalfaxan (1 mg·kg$^{-1}$), and maintained by intubating 2% isoflurane during surgery. All animals were ventilated and monitored throughout the surgical procedure. Proximal and distal portions of the femoral artery were temporarily fixed, and each test graft material was inserted into the femoral artery through a transverse incision, and then sutured with 6-0 Prolene suture (Ethicon Inc.), resulting in anastomosis. On day 18 after surgery, blood flow patency was visualized using pulsed-wave Doppler ultrasonography (S22V, SonoScape Medical Co.) and angiography (C-arm radiograph system, OEC Series 9600, GE Healthcare). For angiography, a 4-Fr vascular sheath (Supersheath, Medikit Co. Ltd.) was inserted into the abdominal aorta, and then a non-ionic contrast (Omnipaque 300, Nycomed, Inc) was injected. Afterward, the pig was killed, the femoral artery was recovered, and then histological analysis was performed.

For the histological analysis, the obtained femoral artery was fixed with 10% formalin, embedded in paraffin wax, and then sliced into 4-μm-thick slices, followed by H&E staining. For quantitative analysis of a patency structural factor, tissue sections were subjected to Movat pentachrome staining (Russell-Movat Pentachrome Stain Kit, American MasterTech).

EC dysfunction and inflammation activation analyses were measured by immunostaining of COX-2, VCAM-1 and vWF. A tissue section was deparaffinized with xylene and rehydrated with a 0.1% (w/v) bovine serum albumin (BSA) solution in DPBS for 10 minutes at room temperature (~25° C.). Heat-mediated antigen detection was performed by incubating the tissue section with a citric acid buffer (10 mmol, pH 6.0) at 95° C. for 40 minutes. The section was blocked with a 5% (w/v) BSA solution for 1 hour at room temperature (~25° C.), and then absorbed 0.5% Triton X-100 for 10 minutes. Subsequently, the tissue section was incubated with a primary antibody of each of COX-2, VCAM-1 and vWF at 4° C. overnight, and reacted with Alexa Fluor™ 594-conjugated goat anti-mouse IgG as a secondary antibody (1:500 dilution, Invitrogen). The primary antibody (1:100 dilution, Invitrogen) included a mouse anti-COX-2 monoclonal antibody, a mouse anti-VCAM-1 monoclonal antibody and a mouse anti-vWF monoclonal antibody. After staining an α-SMA with an anti-SMA polyclonal antibody (1:100 dilution, Abcam), smooth muscle cells were identified by incubation with Alexa Fluor™ 488-conjugated goat anti-rabbit IgG (1:500 dilution, Invitrogen). The nucleus was counter-stained with 4',6-diamidino-2-phenylindole (DAPI), and subjected to ImageJ analysis through confocal imaging (LSM700).

Through the Doppler ultrasonic imaging, in a direct stepped model, blood flow patency was not observed. However, from 1 to 18 days after transplantation, in a diffuser model, maximum blood flow patency was maintained (FIG. 24A). This fact was supported by a higher flow rate compared to the normal femoral artery and the direct stepped model (FIG. 24B). From the angiography result, there was almost no blood flow patency in the direct stepped model, but normal pulsating blood flow was clearly confirmed in the diffuser model (FIG. 24C). It was expected that these results are caused by obstructive formation of stenotic lesions through thrombosis and inflammatory reactions at the proximal and distal sites of the femoral artery in the direct stepped model (FIGS. 24D and 24E).

The above-described expectation for the pathological reactions was demonstrated by confirming that expression is highly increased in the case of a direct stepped graft material, contrary to a diffuser graft material showing a histological characteristic similar to a normal blood vessel in terms of a protein marker expression pattern involved in inflammatory reactions (cyclooxygenase-2 (COX-2) and vascular cell adhesion protein-1 (VCAM-1)), EC thrombosis (Willebrand factor (vWF) and the location of smooth muscle cells (smooth muscle actin (SMA)) (FIG. 24F).

[Description of reference numerals]

| | |
|---|---|
| 10: Damaged site of blood vessel | |
| 11: Blood vessel, first blood vessel | 12: Second blood vessel |
| 13: Blood vessel perforation | |
| 100: Vascular anastomotic member | |
| 101: Perforation | 110: Fixing protrusion |
| 200: Branch tube | |
| 201: Inner diameter | 210: Guide protrusion |

What is claimed is:

1. A vascular anastomotic member comprising a shape-memory polymer represented by Formula 1 below:

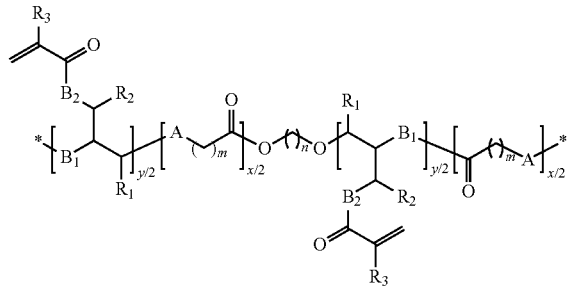

[Formula 1]

wherein, in Formula 1, $R_1$, $R_2$ and $R_3$ are each independently hydrogen (H) or a C1 to C6 alkyl group, m and n are each independently an integer of 1 to 20, A, $B_1$ and $B_2$ are each independently oxygen (O) or sulfur(S), x and y represent mol % of a repeat unit, x+y is 100, and x is 80 to 95.

2. The vascular anastomotic member of claim 1, wherein, in Formula 1, $R_1$, $R_2$ and $R_3$ are each independently hydrogen (H) or a methyl group, m and n are each independently an integer of 3 to 12, A, $B_1$ and $B_2$ are each independently oxygen (O) or sulfur(S), x and y represent mol % of a repeat unit, x+y is 100, and x is 88 to 94.

3. The vascular anastomotic member of claim 1, wherein the shape-memory polymer has a melting temperature of 30 to 48° C. on average.

4. The vascular anastomotic member of claim 1, wherein the shape-memory polymer has an average melting temperature of 28 to 42° C. after crosslinking.

5. The vascular anastomotic member of claim 1, comprising a shape-memory polymer represented by Formula 2:

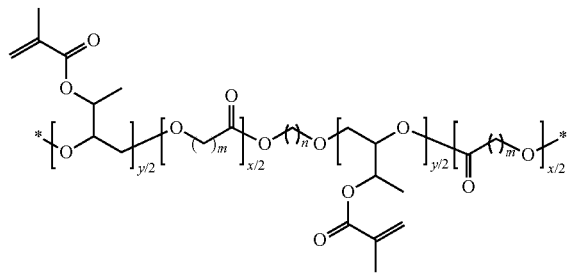

[Formula 2]

wherein, in Formula 2, m and n are each independently an integer of 1 to 20, x and y represent mol % of a repeat unit, x+y is 100, and x is 80 to 95.

6. The vascular anastomotic member of claim 1, wherein the vascular anastomotic member has a tubular shape inserted into ends of a first blood vessel and a second blood vessel.

7. The vascular anastomotic member of claim 6, wherein the vascular anastomotic member is changed according to the inner diameters of the first blood vessel and the second blood vessel at 28 to 42° C. or more on average.

8. The vascular anastomotic member of claim 6, wherein the vascular anastomotic member has a sectional thickness of 50 to 200 μm.

9. The vascular anastomotic member of claim 6, wherein the vascular anastomotic member has an inner diameter of 0.2 to 5 mm, and the inner diameter of the vascular anastomotic member gradually increases from a first direction to a second direction.

10. The vascular anastomotic member of claim 6, comprising:
 a plurality of fixing protrusions fixed to a blood vessel on an outer circumference surface of the vascular anastomotic member.

11. The vascular anastomotic member of claim 1, wherein the vascular anastomotic member has a sheet shape surrounding a damaged site of a blood vessel, and whose shape is changed to surround an outer diameter of the blood vessel at 28 to 42° C. or more on average.

12. The vascular anastomotic member of claim 11, wherein a perforation is formed in one area of the vascular anastomotic member, and a branch tube is integrally connected to an area corresponding to the perforation.

13. The vascular anastomotic member of claim 12, wherein an inner diameters of the perforation and the branch tube correspond to each other, and the branch tube is configured to communicate with the damaged site of the blood vessel.

14. The vascular anastomotic member of claim 12, wherein the branch tube has a guide protrusion on an inner circumference surface, and the guide protrusion is expanded in a longitudinal direction along the axis of the branch tube.

15. The vascular anastomotic member of claim 12, wherein the branch tube comprises one or more types of biocompatible polymers selected from the group consisting of polyethylene glycol, polyglycolide, poly-L-lactide, poly-D,L-lactide, poly(lactide-co-glycolide) and hyaluronic acid.

16. The vascular anastomotic member of claim 11, comprising:
 a plurality of protrusions which are located on a back side of the vascular anastomotic member and configured to be fixed to the blood vessel.

17. The vascular anastomotic member of claim 1, wherein the vascular anastomotic member comprises an antithrombotic material.

* * * * *